(12) United States Patent
Kloti et al.

(10) Patent No.: US 6,696,621 B2
(45) Date of Patent: Feb. 24, 2004

(54) SELECTABLE MARKER IN PLANTS

(75) Inventors: Andreas S. Kloti, Durham, NC (US); Keith R. Davis, Durham, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 09/792,568

(22) Filed: Feb. 23, 2001

(65) Prior Publication Data

US 2003/0167501 A1 Sep. 4, 2003

(51) Int. Cl.⁷ .................. C12N 15/82; C12N 15/52; C12N 5/04
(52) U.S. Cl. .................. 800/288; 435/420; 435/468
(58) Field of Search .................. 435/69.1, 455, 435/468, 471, 420; 800/278, 288

(56) References Cited

U.S. PATENT DOCUMENTS 6,027,900 A    2/2000   Allnutt et al.

FOREIGN PATENT DOCUMENTS

WO    9741228    11/1997

OTHER PUBLICATIONS

Anderson WF.Human gene therapy. Nature. 1998 Apr 30;392(6679 Suppl):25–30. Review.*
Krugel et al. (1993) Gene 127, 127–131. *Sequence and Transcriptional Analysis of the Nourseothricin Acetyltransferase–Encoding Gene nat1 from Streptomyces Noursei.*
Werner BioAgents Gisela Werner e.Kfr., Meisenweg 7, D–07751, Jena–Cospeda/Germany http://www.webioage.com.

* cited by examiner

*Primary Examiner*—Phuong T. Bui
*Assistant Examiner*—Cynthia Collins
(74) *Attorney, Agent, or Firm*—Laura L. Kiefer; Timothy G. Hofmeyer; Deborah H. Spencer

(57) ABSTRACT

Novel protein useful as a selectable marker resistant to the antibiotic nourseothricin and corresponding polynucleotides for insertion of genes and other genetic material into a variety of organisms, including plants are described.

18 Claims, 5 Drawing Sheets

D: n=3
F: n=1

SELECTABLE MARKER IN PLANTS

FIELD OF THE INVENTION

The present invention relates to a novel protein useful as a selectable marker and corresponding polynucleotides for insertion of genes and other genetic material into a variety of organisms, including plants.

BACKGROUND OF THE INVENTION

Selectable markers are genes that impart a characteristic to an organism to see the results of a biochemical or chemical assay or test. Such markers are known as labels. One of the basic principles of recombinant DNA technology is the use of biological markers to identify cells carrying recombinant DNA molecules. In bacteria, these are commonly drug resistance genes. In bacteria, drug resistance is used to select bacteria that have taken up cloned DNA from the much larger population of bacteria that have not. For example, a commonly used marker in mammalian cells is a bacterial drug-resistance gene that confers resistance to a neomycin-related drug, G418, which kills mammalian cells by blocking protein synthesis. The marker gene encodes an enzyme that destroys the drug. Although numerous markers exist for bacterial and mammalian cells, fewer gene markers are available for organisms such as plants. It would be desirable to provide a gene marker that could enable one to differentiate between plants that carry particular recombinant DNA molecules from plant that do not.

SUMMARY OF THE INVENTION

In one embodiment, the present invention is directed towards a nucleic acid sequence comprising a polynucleotide encoding a protein comprising the amino acid sequence of SEQ ID. NO. 1. The nucleic acid sequence may be selected from the group consisting of SEQ ID NOS. 2, 3 and 4.

In another embodiment, the present invention is directed toward a DNA construct comprising a nucleic acid sequence comprising a polynucleotide encoding a protein comprising the amino acid sequence of SEQ ID. NO. 1.

In another embodiment, the present invention is directed towards a plasmid comprising a nucleic acid sequence comprising a polynucleotide encoding a protein comprising the amino acid sequence of SEQ ID. NO. 1.

In another embodiment, the present invention is directed towards a eukaryotic cell comprising a nucleic acid sequence comprising a polynucleotide encoding a protein comprising the amino acid sequence of SEQ ID. NO. 1. The eukaryotic cell can be a plant cell, such as a dicot plant cell or a monocot plant cell.

In another embodiment, the present invention is directed toward a plant or plant part having a eukaryotic cell comprising a nucleic acid sequence comprising a polynucleotide encoding a protein comprising the amino acid sequence of SEQ ID. NO. 1.

In another embodiment, the present invention is directed toward seed that can produce a plant comprising a nucleic acid sequence comprising a polynucleotide encoding a protein comprising the amino acid sequence of SEQ ID. NO. 1. The present invention is also directed towards seed from the plant of this embodiment.

In another embodiment, the present invention is directed toward a method of conferring resistance to the antibiotic nourseothricin, comprising providing to an organism t a nucleic acid sequence comprising a polynucleotide encoding a protein comprising the amino acid sequence of SEQ ID. NO. 1.

In another embodiment, the present invention is directed toward a protein either comprising or consisting of the amino acid sequence of SEQ ID. NO. 1. The protein can be in an isolated or non-isolated form.

In another embodiment, the present invention is directed towards a eukaryotic cell that can express a protein either comprising or consisting of the amino acid sequence of SEQ ID. NO. 1.

In another embodiment, the present invention a plant or plant part having a eukaryotic cell that can express a protein either comprising or consisting of the amino acid sequence of SEQ ID. NO. 1.

In another embodiment, the present invention is directed towards seed that can produce a plant comprising a protein either comprising or consisting of the amino acid sequence of SEQ ID. NO. 1.

In any of the above embodiments, the eukaryotic cells, plant or plant part can be from an organism such as a microorganism or a plant, such as a dicot plant, e.g. *Arabidopsis thaliana* or a monocot plant, e.g. *Oryza sativa*.

DETAILED DESCRIPTION OF THE INVENTION

Figure 1:
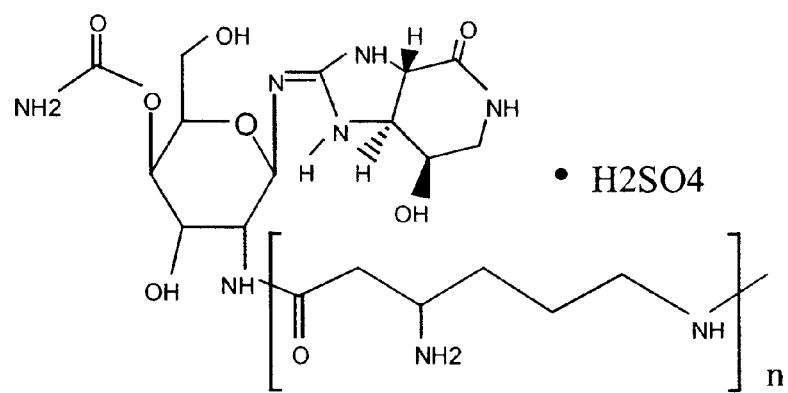
FIG. 1. is a represenation of the structure of the molecule "clonNAT". ClonNAT is the dihydrogen sulphate of the weakly basic antibiotic nourseothricin, consisting of streptothricin components F and D. The chemical name is 2-[4-O-Carbamoyl-2-deoxy-2-(3,6-diaminohexan-amido)-B-D-gulopyranoslamino)-3,3a,5 ,6,7,7a-hexahydro-5-hydroxy-4H-imidazo[4,5-c]pyridin-4one dihydrogensulphate.

This invention describes the use of a novel nourseothricin N-acetyltransferase (NRG) with the aminoacid sequence SEQ. ID No. 1, encoded by a novel nucleotide sequence as exemplified, but not limited to SEQ. ID Nos. 2, 3 and 4, useful as a selectable marker in an organism such as microorganisms and plants. The conditions for its use as selectable marker with rice and *Arabidopsis thaliana* are described herein.

Unless otherwise defined, technical and scientific terms used herein have the same meaning as commonly understood by one of ordinary skill in the art to which this invention belongs.

Ag7 term—the Ag7 terminator sequence is a sequence of 213 nucleotides from the 3' end of the gene number 7 from *Agrobacterium tumefaciens*. The sequence is derived from plasmid vector pGPTV-HPT as described by Becker et al. in 1992 (Plant Mol Biol 20:1195–1197).

aph4—selectable marker gene for hygromycin resistance. The sequence is derived from plasmid vector pGPTV-HPT as described by Becker et al. in 1992 (Plant Mol Biol 20:1195–1197).

AvrII refers to a restriction enzyme site. "clonNAT" is the dihydrogen sulphate of the weakly basic antibiotic nourseothricin, consisting of streptothricin components F and D. The chemical name is 2-[4O-Carbamoyl-2-deoxy-2-(3,6-diaminohexan-amido)-B-D-gulopyranoslamino)3,3a,5,6,7,7a-hexahydro-5-hydroxy4H-imidazo [4,5-c]pyridin-4-one dihydrogensulphate. GUS Intron refers to the GUS marker gene containing an intron, as disclosed in plamids pPG361 and pPG363.

HindIII refers to a restriction enzyme site.

nos prom—a promoter sequence from the nopaline synthase gene of *Agrobacterium tumefaciens*, as disclosed in plasmids pPG354, pPG361, pPG362, pPG363.

nos term—a terminator sequence from the nopaline synthase gene of *Agrobacterium tumefaciens*, as disclosed in plasmids pPG354, pPG361, pPG362, pPG363.

"Nourseothricin" refers to the streptothricin antibiotic components F and D, produced in cultures from a strain of *Streptomyces noursei*.

"nrg gene" refers to a generic group of nucleic acid sequence that can encode for the NRG protein. Selected species of the genus include, but are not limited to, nrg1, nrg2 and nrg3 described herein.

"NRG protein" or "Nourseothricin Resistance Gene protein" refers to the polypeptide or amino acid sequence of SEQ ID. NO. 1. This protein has the ability to confer resistance to the antibiotic known as nourseothricin.

35S prom—a promoter sequence from the genome of cauliflower mosaic virus, as disclosed in plasmids pPG361 and pPG363.

ocs LB or "Left Border" refers to the DNA sequence that flanks the "left end" of the T-DNA and is disclosed in pPG361 and pPG363. The ocs LB is derived from octopine synthase (ocs) tumor inducing plasmids of *Agrobacterium tumefaciens*.

ocs RB or "Right Border" refers to the DNA sequence that flanks the "right end" of the T-DNA and is disclosed in pPG361 and pPG363. The ocs LB is derived from octopine synthase (ocs) tumor inducing plasmids of *Agrobacterium tumefaciens*. The osc RB and osc LB are recognized by Agrobacterium as sites for "cutting" or excision to enable the T-DNA to be inserted into a plant cell.

PmlI refers to a restriction enzyme site.

The microorganism can be, for example, a fungus or bacteria. Where the organism is a fungus, the fungus can be from, but not limited to, any of the following genera: Magnaporthe, Mycosphaerella, Candida, Botrytis, Saccharomyces, Aspergillus, Peronaspora, Sclerotinia, Rhizoctonia, Phythium, Puccinia, Erysiphe, Ustilago, Fusarium, Phytophthora and Penicillium. Where the organism is a bacteria, the bacteria can be from Agrobacterium, Escherichia, Xanthomonas, Staphlococcus, Pseudomonas, Streptomyces and Bacillus.

The following examples are put forth so as to provide those of ordinary skill in the art with a complete disclosure and description of how to make and use the present invention, and is not intended to limit the scope of the invention.

EXAMPLE 1

Preparation of the nrg Gene and Protein

Using the nat1 gene as the staring material from the plasmid pINS1, as delivered from the Hans Knoell Institute, the nrg gene is obtained in a PCR reaction, using the following primers:

forward primer: 5'nat1HindIII; ccgaagcttATGAC-CACTCTTGACGACACG [SEQ ID NO. 5]

reverse primer: 3 'nat1AvrII; aaccctag-gCTAGGGGCAGGGCATGCTCATG [SEQ ID NO. 6]

These primers add a HindIII or a AvrII restriction site right upstream, or downstream of the coding region of the nat1 gene, respectively. The PCR products of two independent reactions are cloned into a pUC vector derived plasmid (pPG354, digested with HindIII and AvrII), adding a nos promoter and a nos terminator upstream, and downstream of the nat1 gene, respectively. The resulting plasmid is called pPG362. The resultant gene is sequenced in the resulting plasmid pPG362 [SEQ ID NO. 7], sequencing three plasmid clones, derived from two independent PCR reactions. Surprisingly and unexpectedly, the sequence of all three clones yields the following new resultant gene, hereafter called the nrg2 gene (SEQ ID NO. 3), with following three nucleotide changes: the nucleotide cytosine ("C") is replaced with adenine ("A") at position 209, the nucleotide guanine ("G") is replaced with adenine ("A") at position 569 and the nucleotide adenine ("A") is replaced with guanine ("G") at position 570. Also surprisingly and unexpectedly, in the resultant NRG protein, the amino acid, glycine (G), is replaced with aspartate (D) at position 70 in the protein or polypeptide sequence. Also surprisingly and unexpectedly, the new NRG protein retains the ability to impart resistance to the nourseothricin antibiotic.

EXAMPLE 2

Cloning the nrg Gene Into a Binary Vector

Figure 2:
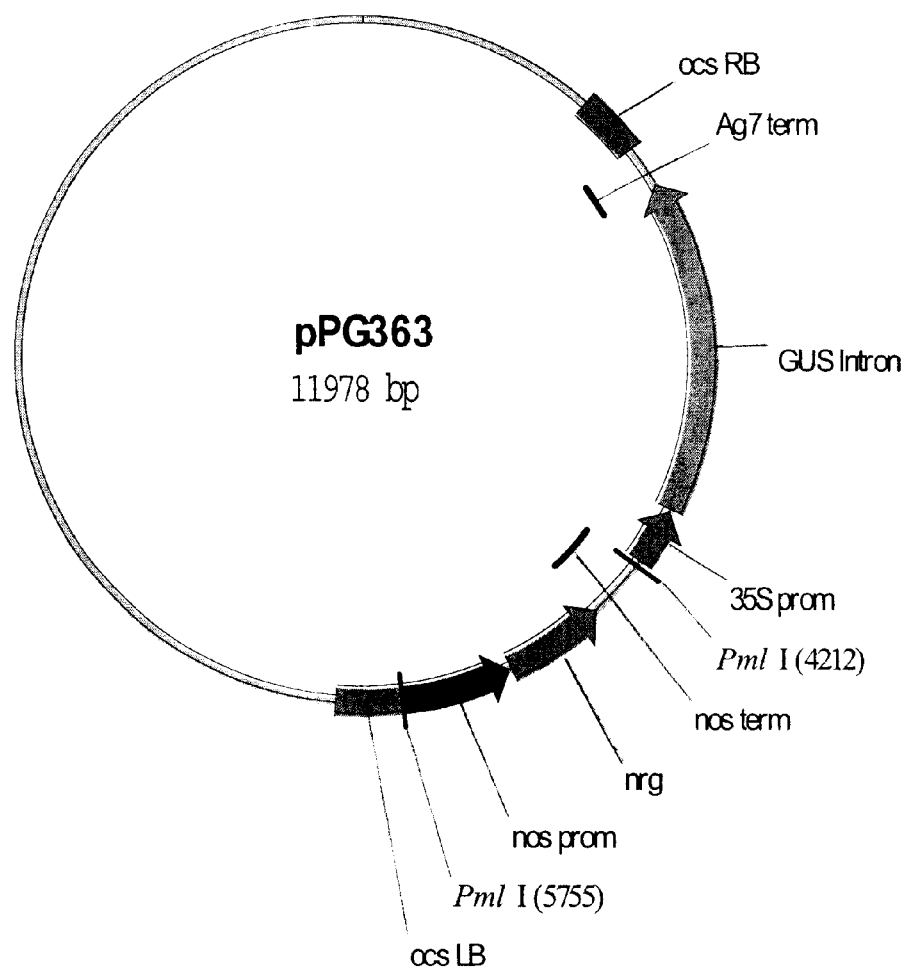
FIG. 2. is a diagram of the plasmid pPG363 (SEQ ID NO. 8) wherein the ocs LB, PmlI, nos prom, nrg, nos term, 35S prom, GUS Intron, Ag7 term, ocs RB are known in the art or described herein. The numbers in parentheses indicate the nucleotide position within the plasmid at which the respective restriction enzymes cut the plasmid DNA.

The nrg gene, controlled by the nos promoter and nos terminator elements from pPG362, is further cloned as a PmlI fragment into the PmlI sites of the binary vector pPG361, replacing the aph4 expression cassette, to give the new vector, pPG363, a binary vector containing the nrg expression cassette. In addition to the nag expression cassette, the pPG363 plasmid [SEQ ID NO. 8] contains pRi Agrobacterium elements, CoLEI elements for replication in *E.coli*, a kanamycin resistance gene, octopine-type left and right T-DNA border elements, and a GUS gene with an intron, controlled by the CaMV 35S promoter and the Ag7 terminator, as presented in FIG. 2.

EXAMPLE 3

Rice Transformation Using a Binary Vector With the nrg Marker Gene a) Dose response. For selection of transgenic calli based on resistance to clonNAT following Agrobacterium-mediated transformation of rice callus material, a dose response experiment is made to determine the concentration of clonNAT in callus growth medium in order to inhibit the growth of rice callus, or to kill the rice cells. Growth media (GM) used for rice callus comprise the following basic components: N6 salts (Duchefa) 3.95 g/l; B5 vitamins (Duchefa) 112 mg/l; proline (Duchefa) 500 mg/l; glutamine (Duchefa) 500 mg/l; casein hydrolysate (Duchefa) 500 mg/l. For the dose response experiment, medium plates are prepared that contain, apart from the basic components (GM), the following components: 2,4-D (2,4-dichlorophenoxyacetic acid; Duchefa) 2 mg/l; maltose (Sigma) 30 g/l; cefotaxime 200 mg/l; agarose (type I, Sigma) 5 g/l; pH 5.6. Medium plates are prepared with 25 ml of filter-sterilized medium per 10 cm petridishes. Variable amounts of a clonNAT stock solution of 200 mg/ml in water is added to these plates before filter-sterilization to obtain medium plates with clonNAT concentrations of 0, 5, 20, 100, 500, 1000 mg/l.

Several pieces of rice callus, derived from immature rice embryos of the variety TP309 (National Small Grain Collection, USDA, ARS, Aberdeen, Id.) are put on these plates, the plates are incubated at 26° C. in the dark, and survival of the embryos and proliferation of the embryo cells are observed every day. Based on the survival rate of the embryos on the media plates containing different concentrations of clonNAT, a useful concentration of clonNAT for selection of transgenic rice is determined to be within a range of about 20 to about 1000 mg/l or more, preferably about 200 mg/l or less.

b) Agrobacterium Transformation. For Agrobacterium-mediated rice transformation, the pPG363 plasmid is electroporated into electroporation-competent Agrobacterium cells of the strain LBA4404 (Life Technologies) and the electroporated cells are plated on LB medium (10 g/l Bactopeptone (Difco), 5 g/l Yeast Extract (Difco), 5 g/l NaCl, 15 g/l Bactoagar (Difco), 50 mg/l kanamycin; pH 7.0) and are incubated at 30° C. Two days after electroporation, a colony is picked from the LB plate and is used to inoculate 5 ml of liquid LB medium (LB medium without Bactoagar). The 5 ml culture is incubated at 30° C. on a shaker at 200 rpm. After 16 hours, 0.05 ml of this 5 ml culture is transferred to 100 ml of liquid LB medium and is then incubated at 30° C. on a shaker at 200 rpm. After 16 hours, the bacteria cells are spun down by centrifugation at 3000 rpm, resuspended in 100 ml of induction medium (GM basic medium with 2,4-D 2 mg/l; 10 g/l glucose; 120 g/l maltose; pH 5.2), and incubated at room temperature on a shaker at 100 rpm. After 1 hour, rice immature embryos that are cultured on GM plates for 6 days after isolation are immersed in the bacteria suspension. After 20 minutes, the embryos are transferred to cocultivation medium plates (GM basic medium with 2,4-D 2 mg/l; 10 g/l glucose; 120 g/l maltose; 50 g/l agarose; pH 5.2) and are incubated for 3 days at 24° C. in the dark The cultivated embryos are transferred to growth medium (GM) plates (GM basic medium with 2,4-D 2 mg/l; maltose 30 g/l; cefotaxime 400 mg/l; agarose 5 g/l; pH 5.6) and incubated at 26° C. in the dark. After 5 days the cultivated embryos are transferred to a selection medium, known as clonNAT200 selection plates (GM basic medium with 2,4-D 2 mg/l; maltose 30 g/l; cefotaxime 200 mg/l; clonNAT 200 mg/l; agarose 5 g/l; pH 5.6) and are incubated at 26° C. in the dark. After 4–5 weeks, colonies of clonNAT-resistant callus are growing from the pieces of embryo-derived callus that died on the clonNAT-containing medium plates. These resistant callus colonies are picked from these plates and are transferred to fresh selection medium with increased maltose concentration (clonNAT200 6%M, GM basic medium with 2,4-D 2 mg/l; maltose 60 g/l; cefotaxime 200 mg/l; clonNAT 200 mg/l; agarose 5 g/l; pH 5.6). Small parts of the isolated callus colonies are used in a histological GUS assay to test for GUS activity. Positive GUS staining is a direct indication that these callus pieces are transgenic (and have been selected on clonNAT selection) with the nrg resistance gene. After 10 days, the resistant calluses are transferred to fresh medium of same composition to increase the callus mass. After 1 week, the callus is transferred to regeneration medium (GM basic medium with maltose 20 g/l; sorbitol 30 g/l; NAA (naphtalene acetic acid) 0.5 mg/l; BAP (6-benzylaminopurine) 3 mg/l; agarose 8 g/l; pH 5.6) and these plates are incubated at 25° C. under 16 hours light. After 4 weeks, small regenerated plantlets are then transferred to rooting medium (½-strength MS (Murashige & Skoog) medium (micro and macro elements and vitamins), 2% sucrose, 0.15% phytagel (Sigma); pH5.6) and grown to a height of 5–10 cm. Such plants are transferred to soil and are grown to maturity in the greenhouse. The transgenic state of these plants is tested by performing a histological GUS assay with leaf tissue, and a Southern analysis with plant genomic DNA probing with the nrg resistance gene.

EXAMPLE 4

*Arabidopsis thaliana* Transformation With the nrg Marker Gene a) Dose response. The selection conditions for plants that are transgenic with the nrg gene are determined in a dose response experiment. From about 2000 to 3000 wildtype *Arabidopsis thaliana* seeds per pot are sown in 5"×5" (13 cm×13 cm) soil pots. When the first true leaves of the seedlings have emerged after approximately 7 days, the seedlings are sprayed with a hand-held sprayer until all leaf material is completely wet on three consecutive days with a solution of 0.005% Silwet L-77 (50 ul/l) in water and variable concentrations of clonNAT (1, 5, 10, 20, 50, 100, 250, 500 mg/l). The results are assessed 36 hours after the last spray. A useful range of concentration of clonNAT for selection of transgenic Arabidopsis plants (as assessed as concentrations that kill non-transgenic Arabidopsis plants after applying the described sprayings) is determined within a range of about 20 to about 1000 mg/l or more, preferably about 200 mg/l or less.

b) *Arabidopsis thaliana* transformation. The binary plasmid pPG363 is transformed into *Agrobacterium tumefaciens* strain, GV3101, and the transformed cells are plated on LB medium (10 g/l Bactopeptone (Difco), 5 g/l Yeast Extract (Difco), 5 g/l NaCl, 15 g/l Bactoagar (Difco), 50 mg/l kanamycin; pH 7.0) and are incubated at 30° C. Two days after transformation, a colony is picked from the LB plate and is used to inoculate 5 ml of liquid LB medium (LB medium without Bactoagar). The 5 ml culture is incubated at 30° C. on a shaker at 200 rpm. After 16 hours, 0.05 ml of this 5 ml culture is transferred to 100 ml of liquid LB medium and is then incubated at 30° C. on a shaker at 200 rpm. For Agrobacterium-mediated transformation of the T-DNA containing the nrg gene and the GUS gene from pPG363 to *Arabidopsis thaliana* via a flower dipping protocol (Clough S J, Bent A F, Floral dip: a simplified method for Agrobacterium-mediated transformation of *Arabidopsis thaliana*. Plant J December, 1998 ; 16(6):735–43), the primary bolts of about five-weeks old *Arabidopsis thaliana* plants are removed. Five days later, subsequently emerged secondary bolts have grown. The leaves and bolts of these plants are dipped or submerged for five minutes in a suspension, consisting of 30 ml of an over-night culture of *Agrobacterium tumefaciens* (ecotype GV3101, containing the binary vector pPG363) in LB medium, diluted 3-fold with a 5% sucrose solution containing 0.005% Silwet L-77. The dipped plants are then kept for over-night in the dark at 22° C. and are then transferred back to a location in the growth room were they grow to maturity under normal growth conditions. The T1 seed is harvested and then used for selection. 2000–3000 seeds are sown on a 5"×5" pot filled with soil and are stratified for 2 days at 4° C. The pots are then transferred to the growth room with 16 hours light and 22° C. The seedlings are sprayed with a solution containing 0.005% Silwet L-77 and 200 mg/l clonNAT on three consecutive days when the first true leaves have emerged. Surviving seedlings are transferred to individual pots one week after selection and are grown to maturity under normal growth conditions. The transgenic state of the plants and their progenies is tested by performing a histological GUS assay using leaf tissue and by performing Southern analysis using genomic DNA isolated from the Arabidopsis plants and probing the DNA blots with a labelled probe from the nrg gene.

Preparation of Starting Materials

Figure 3:
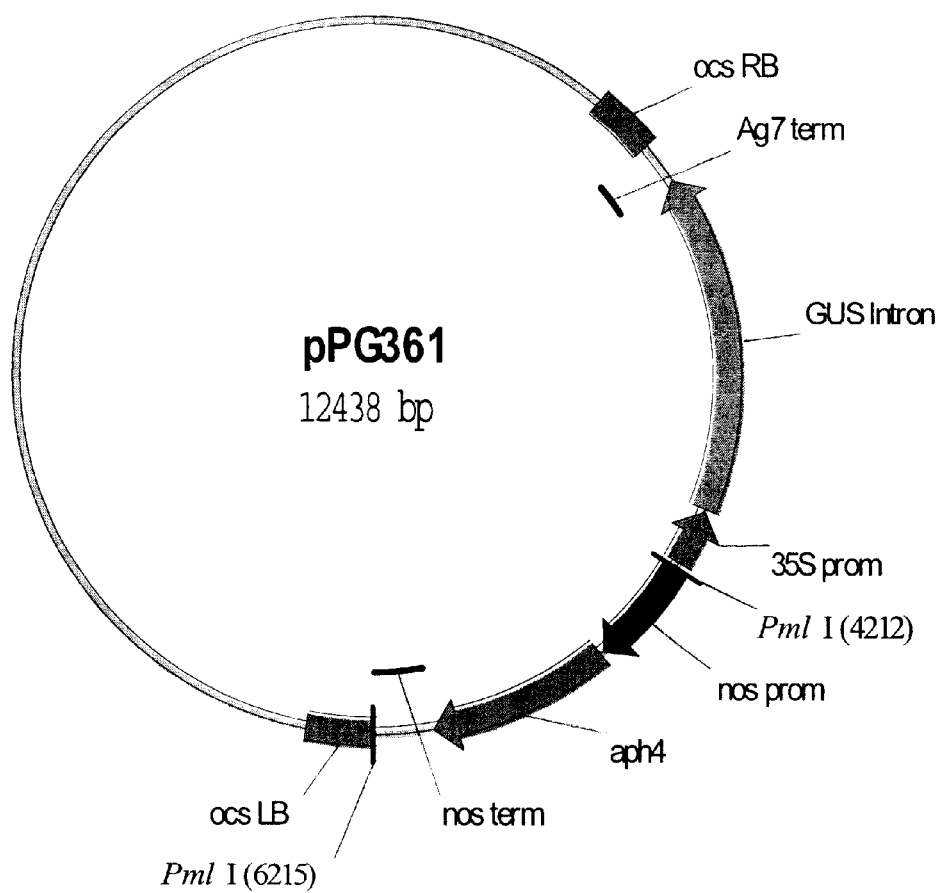
FIG. 3. ia a diagram of the plasmid pPG361 (SEQ ID NO 9) wherein ocs LB, nos term, aph4, nos prom, 35S prom, GUS Intron, Ag7 term, ocs RB, and PmlI are known in the art or as described herein. The numbers in parentheses indicate the nucleotide position within the plasmid at which the respective restriction enzymes cut the plasmid DNA.
Figure 4:
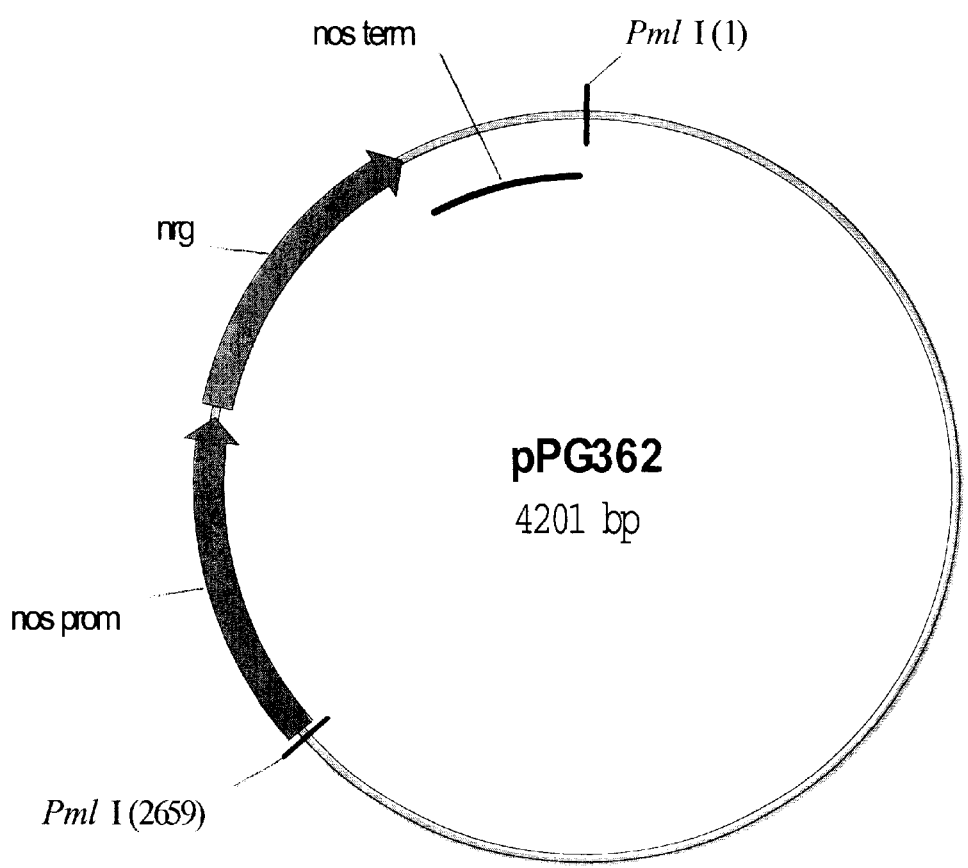
FIG. 4. is a diagram of the plasmid pPG362 (SEQ ID NO 7) wherein the nos prom, the nrg gene, the Nos term, and PmlI are known in the art or described herein. The numbers in parentheses indicate the nucleotide position within the plasmid at which the respective restriction enzymes cut the plasmid DNA.
Figure 5:
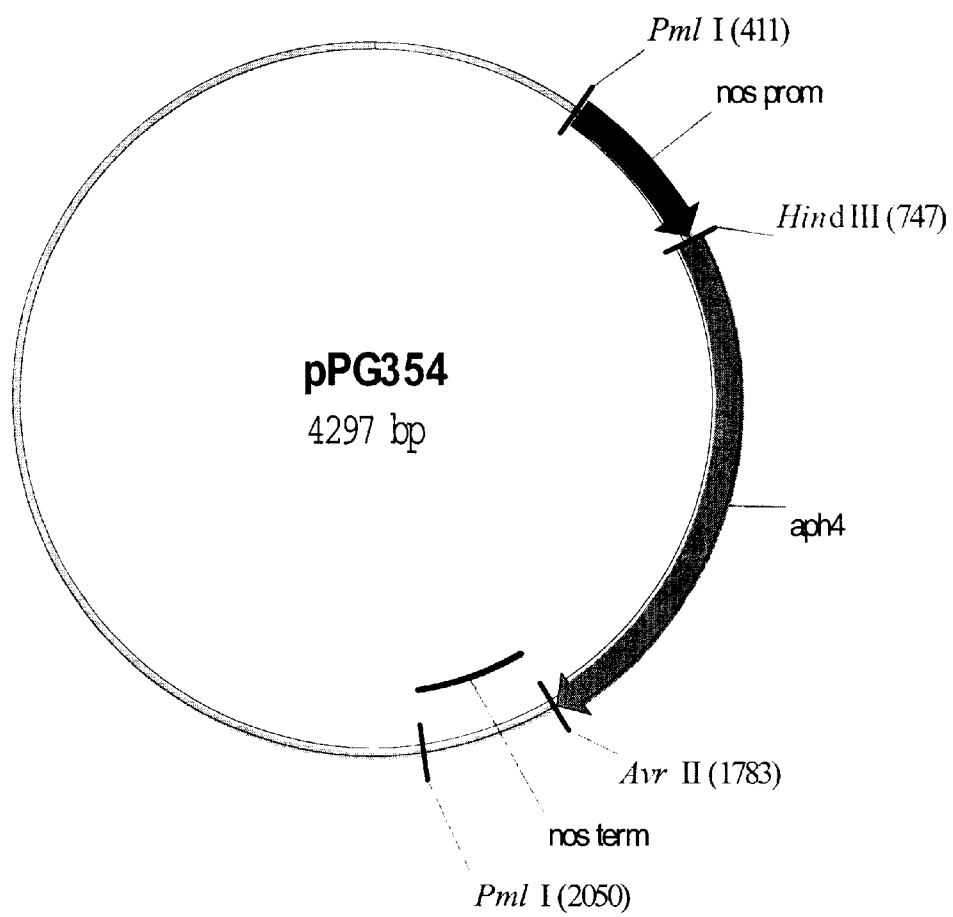
FIG. 5. is a diagram of the plasmid pPG354 (SEQ ID NO 10) wherein nos term, aph4, nos prom, PmlI, HindIII, and AvrII are as known in the art or as described herein. The numbers in parentheses indicate the nucleotide position within the plasmid at which the respective restriction enzymes cut the plasmid DNA.

Origin, cloning, and sequence of the starting materials for preparing the nrg gene. The nat1 gene starting material is obtained from the Hans Knoell Institute, Jena, Germany, in plasmid pINS 1. The sequence of the nat1 gene is described as the sequence X73149.1 (emb|X73149.1|SNNAT1 *S.noursei* gene for nourseothricin acetyltransferase) found in the database at the National Center for Biotechnology Information (NCBI). The binary vector pPG363 (SEQ ID. NO. 8) displayed in FIG. 2 can be prepared from the vectors pPG361 (SEQ ID NO 9) displayed in FIG. 3 and pPG362 (SEQ ID NO. 7) displayed in FIG. 4. Methods for preparing DNA constructs or plasmids is known in the art. See, e.g., Sambrook et al., *Molecular Cloning: A Laboratory Manual* (1989). Plasmid pPG362 (SEQ ID NO. 7) can be prepared from plasmid pPG354 (SEQ ID NO. 10) (FIG. 5) and the nrg gene, as derived from a PCR reaction, by cloning the nrg gene PCR product as HindIII, AvrII-fragment into the HindIII and AvrII restriction sites of pPG354, replacing the aph4 gene.

What is claimed is:

1. A method of conferring resistance to the antibiotic nourseothricin in a plant tissue, comprising:
    a) transforming a plant tissue with a nucleic acid comprising a nucleotide sequence encoding the polypeptide set forth in SEQ ID NO: 1;
    b) exposing the plant tissue to an amount of nourseothricin sufficient to inhibit growth of and/or kill a plant tissue not expressing the polypeptide set forth in SEQ ID NO: 1; and
    c) selecting the transformed plant tissue of step that expresses the polypeptide set forth in SEQ ID NO: 1 by the ability of the transformed plant tissue to grow and/or survive in the presence of the nourseothricin.

2. The method of claim 1 wherein the plant tissue is a monocot plant tissue.

3. The method of claim 1 wherein the plant tissue is a dicot plant tissue.

4. The method of claim 1 wherein the plant tissue is *Arabidopsis thaliana*.

5. The method of claim 1 wherein the plant tissue is *Orzya sativa*.

6. A method for using nourseothricin N-acetyltransferase as a selectable marker of genetic transformation in plants tissue, comprising:
    a) transforming a plant tissue with a nucleic acid comprising a nucleotide sequence encoding the nourseothricin N-acetyltransferase polypeptide set forth in SEQ ID NO: 1;
    b) exposing the plant tissue to an amount of nourseothricin sufficient to inhibit growth of and/or kill a plant tissue not expressing the nourseothricin N-acetyltransferase polypeptide set forth in SEQ ID NO: 1; and
    c) selecting the transformed plant tissue of step (b) that expresses the polypeptide set forth in SEQ ID NO: 1 by the ability of the plant tissue to grow and/or survive in the presence of the nourseothricin, wherein growth and/or survival indicates the plant tissue as being genetically transformed.

7. The method of claim 6 wherein the plant tissue is a monocot plant tissue.

8. The method of claim 6 wherein the plant tissue is a dicot plant tissue.

9. The method of claim 6 wherein the plant tissue is *Arabidopsis thaliana*.

10. The method of claim 6 wherein the plant tissue is *Orzya sativa*.

11. A method of conferring resistance to the antibiotic nourseothricin in a plant, comprising:
    a) transforming a plant with a nucleic acid comprising a polynucleotide sequence encoding the polypeptide set forth in SEQ ID NO: 1;
    b) collecting and sowing the seeds from the plant of step (a);
    c) exposing plants from the sown seeds step (b) to an amount of nourseothricin sufficient to inhibit growth of and/or kill plant not expressing the nourseothricin N-acetyltransferase polypeptide set forth in SEQ ID NO: 1; and
    d) selecting the plant or plants of step (c) that express the polypeptide set forth in SEQ ID NO: 1 by the ability of the plant(s) to grow and/or survive in the presence of the nourseothricin.

12. The method of claim 11 wherein the plant is a monocot.

13. The method of claim 11 wherein the plant is a dicot.

14. The method of claim 11 wherein the plant is *Arabidopsis thaliana*.

15. A method for using nourseothricin N-acetyltransferase as a selectable marker of genetic transformation in plants, comprising:
    a) transforming a plant with a nucleic acid comprising a nucleotide sequence encoding the nourseothricin N-acetyltransferase polypeptide set forth in SEQ ID NO: 1;
    b) collecting and sowing seeds from the plant of step (a);
    d) exposing plants from the sown seeds of step (b) to an amount of nourseothricin sufficient to inhibit growth of and/or kill a plant not expressing the nourseothricin N-acetyltransferase polypeptide set forth in SEQ ID NO: 1; and
    e) selecting the plant or plants of step (c) that express the polypeptide set forth in SEQ ID NO: 1 by the ability of the plant(s) to grow and/or survive in the presence of the nourseothricin, wherein growth and/or survival indicates the plant(s) as being genetically transformed.

16. The method of claim 15 wherein the plant is a monocot.

17. The method of claim 15 wherein the plant is a dicot.

18. The method of claim 15 wherein the plant is *Arabidopsis thaliana*.

* * * * *

SEQUENCE LISTING

```
<160> NUMBER OF SEQ ID NOS:  10

<210> SEQ ID NO 1
<211> LENGTH: 189
<212> TYPE: PRT
<213> ORGANISM: Artificial Sequence
<220> FEATURE:
<223> OTHER INFORMATION: Novel protein conferring resistance to the
      antibiotic known as nourseothricin

<400> SEQUENCE: 1

Met Thr Thr Leu Asp Asp Thr Ala Tyr Arg Tyr Arg Thr Ser Val Pro
1               5                   10                  15

Gly Asp Ala Glu Ala Ile Glu Ala Leu Asp Gly Ser Phe Thr Thr Asp
            20                  25                  30

Thr Val Phe Arg Val Thr Ala Thr Gly Asp Gly Phe Thr Leu Arg Glu
        35                  40                  45

Val Pro Val Asp Pro Pro Leu Thr Lys Val Phe Pro Asp Asp Glu Ser
    50                  55                  60

Asp Asp Glu Ser Asp Asp Gly Glu Asp Gly Asp Pro Asp Ser Arg Thr
65                  70                  75                  80

Phe Val Ala Tyr Gly Asp Asp Gly Asp Leu Ala Gly Phe Val Val Val
                85                  90                  95

Ser Tyr Ser Gly Trp Asn Arg Arg Leu Thr Val Glu Asp Ile Glu Val
            100                 105                 110

Ala Pro Glu His Arg Gly His Gly Val Gly Arg Ala Leu Met Gly Leu
        115                 120                 125

Ala Thr Glu Phe Ala Arg Glu Arg Gly Ala Gly His Leu Trp Leu Glu
    130                 135                 140

Val Thr Asn Val Asn Ala Pro Ala Ile His Ala Tyr Arg Arg Met Gly
145                 150                 155                 160

Phe Thr Leu Cys Gly Leu Asp Thr Ala Leu Tyr Asp Gly Thr Ala Ser
                165                 170                 175
```

Asp Gly Glu Gln Ala Leu Tyr Met Ser Met Pro Cys Pro
         180                 185

<210> SEQ ID NO 2
<211> LENGTH: 570
<212> TYPE: DNA
<213> ORGANISM: Artificial Sequence
<220> FEATURE:
<223> OTHER INFORMATION: nrg1 - codons optimized for NRG (GC content
      46.84%)

<400> SEQUENCE: 2

| | | | | | | |
|---|---|---|---|---|---|---|
| atgactactc | ttgatgatac | tgcttaccgt | taccgtactt | ctgttcctgg | agatgctgag | 60 |
| gctatcgagg | ctcttgatgg | atctttcact | actgatactg | ttttccgtgt | tactgctact | 120 |
| ggagatggat | tcactcttcg | tgaggttcct | gttgatcctc | tcttactaa | ggttttccct | 180 |
| gatgatgagt | ctgatgatga | gtctgatgat | ggagaggatg | gagatcctga | ttctcgtact | 240 |
| ttcgttgctt | acggagatga | tggagatctt | gctggattcg | ttgttgtttc | ttactctgga | 300 |
| tggaaccgtc | gtcttactgt | tgaggatatc | gaggttgctc | ctgagcatcg | tggacatgga | 360 |
| gttggacgtg | ctcttatggg | acttgctact | gagttcgctc | gtgagcgtgg | agctggacat | 420 |
| cttttggcttg | aggttactaa | cgttaacgct | cctgctatcc | atgcttaccg | tcgtatggga | 480 |
| ttcactcttt | gtggacttga | tactgctctt | tacgatggaa | ctgcttctga | tggagagcag | 540 |
| gctctttaca | tgtctatgcc | ttgtccttga | | | | 570 |

<210> SEQ ID NO 3
<211> LENGTH: 570
<212> TYPE: DNA
<213> ORGANISM: Artificial Sequence
<220> FEATURE:
<223> OTHER INFORMATION: nrg2 - codons not optimized for NRG (GC content
      70.70%), after PCR reaction

<400> SEQUENCE: 3

| | | | | | | |
|---|---|---|---|---|---|---|
| atgaccactc | ttgacgacac | ggcttaccgg | taccgcacca | gtgtcccggg | ggacgccgag | 60 |
| gccatcgagg | cactggatgg | gtccttcacc | accgacaccg | tcttccgcgt | caccgccacc | 120 |
| ggggacggct | tcaccctgcg | ggaggtgccg | gtggacccgc | ccctgaccaa | ggtgttcccc | 180 |
| gacgacgaat | cggacgacga | atcggacgac | ggggaggacg | gcgacccgga | ctcccggacg | 240 |
| ttcgtcgcgt | acggggacga | cggcgacctg | gcgggcttcg | tggtcgtctc | gtactccggc | 300 |
| tggaaccgcc | ggctgaccgt | cgaggacatc | gaggtcgccc | cggagcaccg | ggggcacggg | 360 |
| gtcgggcgcg | cgttgatggg | gctcgcgacg | gagttcgccc | gcgagcgggg | cgccgggcac | 420 |
| ctctggctgg | aggtcaccaa | cgtcaacgca | ccggcgatcc | acgcgtaccg | gcggatgggg | 480 |
| ttcaccctct | gcggcctgga | caccgccctg | tacgacggca | ccgcctcgga | cggcgagcag | 540 |
| gcgctctaca | tgagcatgcc | ctgcccctag | | | | 570 |

<210> SEQ ID NO 4
<211> LENGTH: 570
<212> TYPE: DNA
<213> ORGANISM: Artificial Sequence
<220> FEATURE:
<223> OTHER INFORMATION: nrg3 - codons optimized for NRG (GC content
      46.84%)

<400> SEQUENCE: 4

| | | | | | | |
|---|---|---|---|---|---|---|
| atgactactc | ttgatgatac | tgcttaccgt | taccgtactt | ctgttcctgg | agatgctgag | 60 |
| gctatcgagg | ctcttgatgg | atctttcact | actgatactg | ttttccgtgt | tactgctact | 120 |

```
ggagatggat tcactcttcg tgaggttcct gttgatcctc ctcttactaa ggttttccct    180
gatgatgagt ctgatgatga gtctgatgat ggagaggatg gagatcctga ttctcgtact    240
ttcgttgctt acggagatga tggagatctt gctggattcg ttgttgtttc ttactctgga    300
tggaaccgtc gtcttactgt tgaggatatc gaggttgctc ctgagcatcg tggacatgga    360
gttggacgtg ctcttatggg acttgctact gagttcgctc gtgagcgtgg agctggacat    420
ctttggcttg aggttactaa cgttaacgct cctgctatcc atgcttaccg tcgtatggga    480
ttcactcttt gtggacttga tactgctctt tacgatggaa ctgcttctga tggagagcag    540
gctctttaca tgtctatgcc ttgtccttga                                     570

<210> SEQ ID NO 5
<211> LENGTH: 30
<212> TYPE: DNA
<213> ORGANISM: Artificial Sequence
<220> FEATURE:
<223> OTHER INFORMATION: forward primer: 5'nat1HindIII

<400> SEQUENCE: 5
ccgaagctta tgaccactct tgacgacacg                                      30

<210> SEQ ID NO 6
<211> LENGTH: 31
<212> TYPE: DNA
<213> ORGANISM: Artificial Sequence
<220> FEATURE:
<223> OTHER INFORMATION: reverse primer: 3'nat1AvrII

<400> SEQUENCE: 6
aaccctaggc tagggcagg gcatgctcat g                                     31

<210> SEQ ID NO 7
<211> LENGTH: 4201
<212> TYPE: DNA
<213> ORGANISM: Artificial Sequence
<220> FEATURE:
<223> OTHER INFORMATION: plasmid pPG362 with nrg2 gene

<400> SEQUENCE: 7 gtggggata aattcactgg ccgtcgtttt acaacgtcgt gactgggaaa accctggcgt       60
tacccaactt aatcgccttg cagcacatcc ccctttcgcc agctggcgta atagcgaaga    120
ggcccgcacc gatcgccctt cccaacagtt gcgcagcctg aatggcgaat ggcgcctgat    180
gcggtatttt ctccttacgc atctgtgcgg tatttcacac cgcatatggt gcactctcag    240
tacaatctgc tctgatgccg catagttaag ccagccccga cacccgccaa cacccgctga    300
cgcgccctga cgggcttgtc tgctcccggc atccgcttac agacaagctg tgaccgtctc    360
cgggagctgc atgtgtcaga ggttttcacc gtcatcaccg aaacgcgcga cgcgaaaggg    420
cctcgtgata cgcctatttt tataggttaa tgtcatgata ataatggttt cttagacgtc    480
aggtggcact tttcggggaa atgtgcgcgg aaccccctat tgtttatttt tctaaataca    540
ttcaaatatg tatccgctca tgagacaata accctgataa atgcttcaat aatattgaaa    600
aaggaagagt atgagtattc aacatttccg tgtcgccctt attcccttt ttgcggcatt    660 ttgccttcct gtttttgctc acccagaaac gctggtgaaa gtaaaagatg ctgaagatca    720
gttgggtgca cgagtgggtt acatcgaact ggatctcaac agcggtaaga tccttgagag    780
ttttcgcccc gaagaacgtt ttccaatgat gagcactttt aaagttctgc tatgtggcgc    840
```

-continued

```
ggtattatcc cgtattgacg ccgggcaaga gcaactcggt cgccgcatac actattctca    900
gaatgacttg gttgagtact caccagtcac agaaaagcat cttacggatg gcatgacagt    960
aagagaatta tgcagtgctg ccataaccat gagtgataac actgcggcca acttacttct   1020
gacaacgatc ggaggaccga aggagctaac cgcttttttg cacaacatgg gggatcatgt   1080
aactcgcctt gatcgttggg aaccggagct gaatgaagcc ataccaaacg acgagcgtga   1140
caccacgatg cctgtagcaa tggcaacaac gttgcgcaaa ctattaactg gcgaactact   1200
tactctagct tcccggcaac aattaataga ctggatggag gcggataaag ttgcaggacc   1260
acttctgcgc tcggcccttc cggctggctg gtttattgct gataaatctg gagccggtga   1320
gcgtgggtct cgcggtatca ttgcagcact ggggccagat ggtaagccct cccgtatcgt   1380
agttatctac acgacgggga gtcaggcaac tatggatgaa cgaaatagac agatcgctga   1440
gataggtgcc tcactgatta agcattggta actgtcagac caagtttact catatatact   1500
ttagattgat ttaaaacttc atttttaatt taaaaggatc taggtgaaga tcctttttga   1560
taatctcatg accaaaatcc cttaacgtga gttttcgttc cactgagcgt cagaccccgt   1620
agaaaagatc aaaggatctt cttgagatcc ttttttttctg cgcgtaatct gctgcttgca   1680
aacaaaaaaa ccaccgctac cagcggtggt ttgtttgccg gatcaagagc taccaactct   1740
tttttccgaag gtaactggct tcagcagagc gcagatacca aatactgtcc ttctagtgta   1800
gccgtagtta ggccaccact tcaagaactc tgtagcaccg cctacatacc tcgctctgct   1860
aatcctgtta ccagtggctg ctgccagtgg cgataagtcg tgtcttaccg ggttggactc   1920
aagacgatag ttaccggata aggcgcagcg gtcgggctga acggggggtt cgtgcacaca   1980
gcccagcttg gagcgaacga cctacaccga actgagatac ctacagcgtg agctatgaga   2040
aagcgccacg cttcccgaag ggagaaaggc ggacaggtat ccggtaagcg cagggtcgg   2100
aacaggagag cgcacgaggg agcttccagg gggaaacgcc tggtatcttt atagtcctgt   2160
cgggtttcgc cacctctgac ttgagcgtcg atttttgtga tgctcgtcag ggggggcggag   2220
cctatggaaa aacgccagca acgcggcctt tttacggttc ctggccttttt gctggccttt   2280
tgctcacatg ttctttcctg cgttatcccc tgattctgtg gataaccgta ttaccgcctt   2340
tgagtgagct gataccgctc gccgcagccg aacgaccgag cgcagcgagt cagtgagcga   2400
ggaagcggaa gagcgcccaa tacgcaaacc gcctctcccc gcgcgttggc cgattcatta   2460
atgcagctgg cacgacaggt ttcccgactg gaaagcgggc agtgagcgca acgcaattaa   2520
tgtgagttag ctcactcatt aggcacccca ggctttacac tttatgcttc cggctcgtat   2580
gttgtgtgga attgtgagcg gataacaatt tcacacagga aacagctatg accatgatta   2640
cgccaagcta taccccacgt gcgtacgctc gagtcacgct gccgcaagca ctcagggcgc   2700
aagggctgct aaaggaagcg gaacacgtag aaagccagtc gcagaaacg gtgctgaccc   2760
cggatgaatg tcagctactg ggctatctgg acaagggaaa acgcaagcgc aaagagaaag   2820
caggtagctt gcagtgggct tacatggcga tagctagact gggcggtttt atggacagca   2880
agcgaaccgg aattgccagc tggggcgccc tctggtaagg ttgggaagcc ctgcaaagta   2940
aactggatgg ctttcttgcc gccaaggatc tgatggcgca ggggatcaag atcatgagcg   3000
gagaattaag ggagtcacgt tatgacccccc gccgatgacg cgggacaagc cgttttacgt   3060
ttggaactga cagaaccgca acgttgaagg agccactcag ccgcgggttt ctggagttta   3120
atgagctaag cacatacgtc agaaaccatt attgcgcgtt caaaagtcgc ctaaggtcac   3180
tatcagctag caaatatttc ttgtcaaaaa tgctccactg acgttccata aattcccctc   3240
```

```
ggtatccaat tagagtctca tattcactct caatccgtat accatggcta agcttatgac    3300
cactcttgac gacacggctt accggtaccg caccagtgtc ccgggggacg ccgaggccat    3360
cgaggcactg gatgggtcct tcaccaccga caccgtcttc cgcgtcaccg ccaccgggga    3420
cggcttcacc ctgcgggagg tgccggtgga cccgcccctg accaaggtgt tccccgacga    3480
cgaatcggac gacgaatcgg acgacgggga ggacggcgac ccggactccc ggacgttcgt    3540
cgcgtacggg gacgacggcg acctggcggg cttcgtggtc gtctcgtact ccggctggaa    3600
ccgccggctg accgtcgagg acatcgaggt cgccccggga caccggggc acgggtcgg    3660
gcgcgcgttg atgggctcg cgacggagtt cgcccgcgag cggggcgccg ggcacctctg    3720
gctggaggtc accaacgtca acgcaccggc gatccacgcg taccggcgga tggggttcac    3780
cctctgcggc ctggacaccg ccctgtacga cggcaccgcc tcggacggcg agcaggcgct    3840
ctacatgagc atgccctgcc cctagcctag gcaactctcc tggcgcacca tcgtcggcta    3900
cagcctcggg aattgctacc gagctcgaat tccccgatc gttcaaacat ttggcaataa    3960
agtttcttaa gattgaatcc tgttgccggt cttgcgatga ttatcatata atttctgttg    4020
aattacgtta agcatgtaat aattaacatg taatgcatga cgttatttat gagatgggtt    4080
tttatgatta gagtcccgca attatacatt taatacgcga tagaaaacaa aatatagcgc    4140
gcaaactagg ataaattatc gcgcgcggtg tcatctatgt tactagatcg ggaggcctca    4200
c                                                                     4201

<210> SEQ ID NO 8
<211> LENGTH: 11978
<212> TYPE: DNA
<213> ORGANISM: Artificial Sequence
<220> FEATURE:
<223> OTHER INFORMATION: plasmid pPG363 - binary vector with the nrg2
      gene

<400> SEQUENCE: 8
tcccgcttcg ccggcgttaa ctcaagcgat tagatgcact aagcacataa ttgctcacag      60
ccaaactatc aggtcaagtc tgcttttatt attttttaagc gtgcataata agccctacac     120
aaattgggag atatatcatg catgaccaaa atcccttaac gtgagttttc gttccactga     180
gcgtcagacc ccgtagaaaa gatcaaagga tcttcttgag atccttttt tctgcgcgta     240
atctgctgct tgcaaacaaa aaaccaccg ctaccagcgg tggtttgttt gccggatcaa     300
gagctaccaa ctctttttcc gaaggtaact ggcttcagca gagcgcagat accaaatact     360
gtccttctag tgtagccgta gttaggccac cacttcaaga actctgtagc accgcctaca     420
tacctcgctc tgctaatcct gttaccagtg gctgctgcca gtggcgataa gtcgtgtctt     480
accgggttgg actcaagacg atagttaccg gataaggcgc agcggtcggg ctgaacgggg     540
ggttcgtgca cacagcccag cttggagcga acgacctaca ccgaactgag atacctacag     600
cgtgagctat gagaaagcgc cacgcttccc gaagggagaa aggcggacag gtatccggta     660
agcggcaggg tcggaacagg agagcgcacg agggagcttc caggggaaa cgcctggtat     720
ctttatagtc ctgtcgggtt tcgccacctc tgacttgagc gtcgattttt gtgatgctcg     780
tcagggggc ggagcctatg gaaaaacgcc agcaacgcgg ccttttacg gttcctggcc     840
ttttgctggc cttttgctca catgttcttt cctgcgttat cccctgattc tgtggataac     900
cgtattaccg cctttgagtg agctgatacc gctcgccgca gccgaacgac cgagcgcagc     960
gagtcagtga gcgaggaagc ggaagagcgc ctgatgcggt attttctcct tacgcatctg    1020
```

```
tgcggtattt cacaccgcat atggtgcact ctcagtacaa tctgctctga tgccgcatag    1080
ttaagccagt atacactccg ctatcgctac gtgactgggt catggctgcg ccccgacacc    1140
cgccaacacc cgctgacgcg ccctgacggg cttgtctgct cccggcatcc gcttacagac    1200
aagctgtgac cgtctccggg agctgcatgt gtcagaggtt ttcaccgtca tcaccgaaac    1260
gcgcgaggca gggtgccttg atgtgggcgc cggcggtcga gtggcgacgg cgcggcttgt    1320
ccgcgccctg gtagagcccg ggcgggtgtt ctgtcgtctc gttgtacaac gaaatccatt    1380
cccattccgc gctcaagatg gcttcccctc ggcagttcat cagggctaaa tcaatctagc    1440
cgacttgtcc ggtgaaatgg gctgcactcc aacagaaaca atcaaacaaa catacacagc    1500
gacttattca cacgagctca aattacaacg gtatatatcc tgccagtcag catcatcaca    1560
ccaaaagtta ggcccgaata gtttgaaatt agaaagctcg caattgaggt ctacaggcca    1620
aattcgctct tagccgtaca atattactca ccggtgcgat gcccccatc gtaggtgaag    1680 gtggaaatta atgatccatc ttgtctagag gcgcgccagg cctccatctt gaaagaaata    1740
tagtttaaat atttattgat aaaataagtc aggtattata gtccaagcaa aacataatt    1800 tattgatgca aagtttaaat tcagaaatat ttcaataact gattatatca gctggtacat    1860
tgccgtagat gaaagactga gtgcgatatt atgtgtaata cataaattga tgatatagct    1920
agcttagctc atcgggccta ggtcattgtt tgcctccctg ctgcggtttt tcaccgaagt    1980
tcatgccagt ccagcgtttt tgcagcagaa aagccgccga cttcggtttg cggtcgcgag    2040
tgaagatccc tttcttgtta ccgccaacgc gcaatatgcc ttgcgaggtc gcaaaatcgg    2100
cgaaattcca tacctgttca ccgacgacgg cgctgacgcg atcaaagacg cggtgataca    2160
tatccagcca tgcacactga tactcttcac tccacatgtc ggtgtacatt gagtgcagcc    2220
cggctaacgt atccacgccg tattcggtga tgataatcgg ctgatgcagt ttctcctgcc    2280
aggccagaag ttctttttcc agtaccttct ctgccgtttc caaatcgccg ctttggacat    2340
accatccgta ataacggttc aggcacagca catcaaagag atcgctgatg gtatcggtgt    2400
gagcgtcgca gaacattaca ttgacgcagg tgatcggacg cgtcgggtcg agtttacgcg    2460
ttgcttccgc cagtggcgcg aaatattccc gtgcaccttg cggacgggta tccggttcgt    2520
tggcaatact ccacatcacc acgcttgggt ggtttttgtc acgcgctatc agctctttaa    2580
tcgcctgtaa gtgcgcttgc tgagtttccc cgttgactgc ctcttcgctg tacagttctt    2640
tcggcttgtt gcccgcttcg aaaccaatgc ctaaagagag gttaaagccg acagcagcag    2700
tttcatcaat caccacgatg ccatgttcat ctgcccagtc gagcatctct tcagcgtaag    2760
ggtaatgcga ggtacggtag gagttggccc caatccagtc cattaatgcg tggtcgtgca    2820
ccatcagcac gttatcgaat cctttgccac gcaagtccgc atcttcatga cgaccaaagc    2880
cagtaaagta gaacggtttg tggttaatca ggaactgttc gcccttcact gccactgacc    2940
ggatgccgac gcgaagcggg tagatatcac actctgtctg cttttggct gtgacgcaca    3000 gttcatagag ataaccttca cccggttgcc agaggtgcgg attcaccact tgcaaagtcc    3060
cgctagtgcc ttgtccagtt gcaaccacct gttgatccgc atcacgcagt caacgctga    3120 catcaccatt ggccaccacc tgccagtcaa cagacgcgtg gttacagtct tgcgcgacat    3180
gcgtcaccac ggtgatatcg tccacccagg tgttcggcgt ggtgtagagc attacgctgc    3240
gatggattcc ggcatagtta aagaaatcat ggaagtaaga ctgcttttc ttgccgtttt    3300 cgtcggtaat caccattccc ggcgggatag tctgccagtt cagttcgttg ttcacacaaa    3360
```

-continued

```
cggtgatacg tacactttc ccggcaataa catacggcgt gacatcggct tcaaatggcg    3420
tatagccgcc ctgatgctcc atcacttcct gattattgac ccacactttg ccgtaatgag    3480
tgaccgcatc gaaacgcagc acgatacgct ggcctgccca acctttcggt ataaagactt    3540
cgcgctgata ccagacgttg cccgcataat tacgaatatc tgcatcggcg aactgatcgt    3600
taaaactgcc tggcacagca attgcccggc tttcttgtaa cgcgctttcc caccaacgct    3660
gatcaattcc acagttttcg cgatccagac tgaatgccca caggccgtcg agttttttga    3720
tttcccgggt tggggtttct acctgaatta atttaccacg gttaatactc agatcaagat    3780
ggtaaaaaaa tggcggtaag attaatctgc acactgtaat taataatgta ccggacgtaa    3840
catatgaagc ttagccatgg gtgatttcag cgtgtcctct ccaaatgaaa tgaacttcct    3900
tatatagagg aagggtcttg cgaaggatag tgggattgtg cgtcatccct tacgtcagtg    3960
gagatatcac atcaatccac ttgctttgaa gacgtggttg gaacgtcttc tttttccacg    4020
atgctcctcg tgggtggggg tccatctttg ggaccactgt cggcagaggc atcttgaacg    4080
atagcctttc ctttatcgca atgatggcat ttgtagtgcc accttccttt tctactgtcc    4140
ttttgatgaa gtgacagata ggatcgggaa ttaattcgga tccgtacggc gcgccgcgcc    4200
atttaaatca cgtgaggcct cccgatctag taacatagat gacaccgcgc gcgataattt    4260
atcctagttt gcgcgctata ttttgttttc tatcgcgtat taaatgtata attgcgggac    4320
tctaatcata aaaacccatc tcataaataa cgtcatgcat tacatgttaa ttattacatg    4380
cttaacgtaa ttcaacagaa attatatgat aatcatcgca agaccggcaa caggattcaa    4440
tcttaagaaa ctttattgcc aaatgtttga acgatcgggg aaattcgagc tcggtagcaa    4500
ttcccgaggc tgtagccgac gatggtgcgc caggagagtt gcctaggcta ggggcagggc    4560
atgctcatgt agagcgcctg ctcgccgtcc gaggcggtgc cgtcgtacag ggcggtgtcc    4620
aggccgcaga gggtgaaccc catccgccgg tacgcgtgga tcgccggtgc gttgacgttg    4680
gtgacctcca gccagaggtg cccggcgccc cgctcgcggg cgaactccgt cgcgagcccc    4740
atcaacgcgc gcccgacccc gtgccccggg tgctccgggg cgacctcgat gtcctcgacg    4800
gtcagccggc ggttccagcc ggagtacgag acgaccacga agcccgccag gtcgccgtcg    4860
tccccgtacg cgacgaacgt ccgggagtcc gggtcgccgt cctccccgtc gtccgattcg    4920
tcgtccgatt cgtcgtcggg gaacaccttg gtcagggcg gtccaccgg cacctcccgc    4980 agggtgaagc cgtccccggt ggcggtgacg cggaagacgg tgtcggtggt gaaggaccca    5040
tccagtgcct cgatggcctc ggcgtccccc gggacactgg tgcggtaccg gtaagccgtg    5100
tcgtcaagag tggtcataag cttagccatg gtatacggat tgagagtgaa tatgagactc    5160
taattggata ccgaggggaa tttatggaac gtcagtggag cattttgac aagaaatatt    5220 tgctagctga tagtgacctt aggcgacttt tgaacgcgca ataatggttt ctgacgtatg    5280
tgcttagctc attaaactcc agaaacccgc ggctgagtgg ctccttcaac gttgcggttc    5340
tgtcagttcc aaacgtaaaa cggcttgtcc cgcgtcatcg gcggggtca taacgtgact    5400 cccttaattc tccgctcatg atcttgatcc cctgcgccat cagatccttg gcggcaagaa    5460
agccatccag tttactttgc agggcttccc aaccttacca gagggcgccc cagctggcaa    5520
ttccggttcg cttgctgtcc ataaaaccgc ccagtctagc tatcgccatg taagcccact    5580
gcaagctacc tgctttctct ttgcgcttgc gttttccctt gtccagatag cccagtagct    5640
gacattcatc cggggtcagc accgtttctg cggactggct ttctacgtgt tccgcttcct    5700
ttagcagccc ttgcgccctg agtgcttgcg gcagcgtgac tcgagcgtac gcacgtgggt    5760
```

-continued

```
cctattttat aataacgctg cggacatcta cattttttgaa ttgaaaaaaa attggtaatt    5820
actctttctt tttctccata ttgaccatca tactcattgc tgatccatgt agatttcccg    5880
gacatgaagc catttacaat tgaatatatc ctgccgccgc tgccgctttg cacccggtgg    5940
agcttgcatg ttggtttcta cgcagaactg agccggttag gcagataatt ccattgaga    6000
actgagccat gtgcaccttc ccccaacac ggtgagcgac ggggcaacgg agtgatccac    6060
atgggacttt taaacatcat ccgtcggatg gcgttgcgag agaagcagtc gatccgtgag    6120
atcagccgac gcagcccggg ctgaggtctg cctcgtgaag aaggtgttgc tgactcatac    6180
caggcctgaa tcgccccatc atccagccag aaagtgaggg agccacggtt gatgagagct    6240
ttgttgtagg tggaccagtt ggtgattttg aacttttgct ttgccacgga acggtctgcg    6300
ttgtcgggaa gatgcgtgat ctgatccttc aactcagcaa agttcgatt tattcaacaa    6360
agccgccgtc ccgtcaagtc agcgtaatgc tctgccagtg ttacaaccaa ttaaccaatt    6420
ctgattagaa aaactcatcg agcatcaaat gaaactgcaa tttattcata tcaggattat    6480
caataccata ttttttgaaaa agccgtttct gtaatgaagg agaaaactca ccgaggcagt    6540
tccataggat ggcaagatcc tggtatcggt ctgcgattcc gactcgtcca acatcaatac    6600
aacctattaa tttcccctcg tcaaaaataa ggttatcaag tgagaaatca ccatgagtga    6660
cgactgaatc cggtgagaat ggcaacagct tatgcatttc tttccagact tgttcaacag    6720
gccagccatt acgctcgtca tcaaaatcac tcgcatcaac caaaccgtta ttcattcgtg    6780
attgcgcctg agcgagacga atacgcgat cgctgttaaa aggacaatta caaacaggaa    6840
tcgaatgcaa ccggcgcagg aacactgcca gcgcatcaac aatattttca cctgaatcag    6900
gatattcttc taatacctgg aatgctgttt tcccggggat cgcagtggtg agtaaccatg    6960
catcatcagg agtacggata aaatgcttga tggtcggaag aggcataaat tccgtcagcc    7020
agtttagtct gaccatctca tctgtaacat cattggcaac gctacctttg ccatgtttca    7080
gaaacaactc tggcgcatcg gcttcccat acaatcgata gattgtcgca cctgattgcc    7140
cgacattatc gcgagcccat ttatacccat ataaatcagc atccatgttg gaatttaatc    7200
gcggcctcga gcaagacgtt tcccgttgaa tatggctcat aacaccccctt gtattactgt    7260
ttatgtaagc agacagtttt attgttcatg atgatatatt tttatcttgt gcaatgtaac    7320
atcagagatt ttgagacaca acgaagcttt ctgagccgcc gattttcctc ctcgagttgg    7380
atgaactcgc cgagttcatc gtcaactgaa acagacacgg ccggattctg tgagacaggt    7440
tgaaccgcag ctctcttcca ttgataatag gtctgaacgg aaatacccac gatcttaacg    7500
gcgtccttca aggttgcgcc gccagcgacc tgagcttcga tttgaccgat cttctccagt    7560
ttttctcggt tgctgaggcc gcgggttttc ggcttcacgg atttgaacga tcccgtgcgg    7620
gctgtttcgg ctggtgcttt cttgctctt ctacctctag gagcagccgg ctcaacttcg    7680
gcagcagcag taccgtccgg cggattctgg atctcttcgt cagccattaa tcgtcctctg    7740
tgtgggttat tgctttgtct gccagctcga tccaagagtc aacgtttgtg cctagggcag    7800
taaataggca gtgctccgcg actacatgcc tcggccggca aaataccgcc gcatgtagag    7860
caggctctcc ttcacgatca acgatcggca tggggccttc gtgcttgttg agtaatgtta    7920
tcgctcccat cagagcacgc ttggtactcc gggaatcgga tggtctgtcg atcatccaaa    7980
aaacgctcat gttttcaacc tattaggtct gtggtcagct gaccacagac catcctgctc    8040
catactcgct aattctagcc aaaccgcaac gtcccctgcc cgctagcctt caagagcgcc    8100
```

-continued

| | | | | | |
|---|---|---|---|---|---|
| attatcatcg | ggccaagtga | aaacttcccg | agctcgctcc | gccgtgtcag | atctcggaga | 8160 |
| tagcccccgg | gcgaattgat | gaagttcgct | cgctccaaaa | tgcacgccat | cgctgctgcc | 8220 |
| gcattctccg | gtcccattgc | ctcacacgcg | tcttggtaag | ccgacgggct | gacccccagc | 8280 |
| atagaccgaa | ccaccaccgc | agccgacatg | aggtcacgcc | agctagcaac | cgcaccgctc | 8340 |
| ggcccataat | tgccaatggt | cgggcatgct | ttcaggatca | tcccgagggg | gaacgctttt | 8400 |
| atcggctcgc | tccttgcccg | gtctatttca | ctcggcttag | cgccctgctc | cttttcagag | 8460 |
| cgaggttcaa | gttcattaac | ggattcgggt | tttgaattct | gtatgtgctg | ctcgctctgg | 8520 |
| gcagcattgg | tgctattatt | ttctgaattg | tctctaattt | ccaaccggtt | gattatctct | 8580 |
| tcctggagca | tccacatctc | ttcgagaatt | gactctacat | cagcaagcgt | cggggcgcgt | 8640 |
| ggaattctac | ccacaagttc | cacatagact | tcctcgacag | cttgccagtc | gccctccgct | 8700 |
| ccctcttcca | tagctgccgt | aattagcttc | gaacgtccc | gtcggcaaat | cgtcagactt | 8760 |
| tctttggcca | tcctgaatgc | tgctcgatcg | gccatcacct | gctgtgccat | catcgctagc | 8820 |
| tcttcggacc | gcgcgagaag | cggagacaaa | tcgaagccaa | acgcgcgctc | gatctgacca | 8880 |
| gcgccatcct | tacgagcgta | acgctttccg | ttggcgctat | ccttccggac | gatcaagcct | 8940 |
| gactccacga | gcatggcgat | gtgcctacgc | aaagtcgcgc | cagccatccc | atgcgcccga | 9000 |
| agggcaagct | gagcattcga | cgggaagacg | atcagctgtg | cctcctgacg | caactccgtt | 9060 |
| tccgggtgaa | agctcaatag | cgcatcaagg | acggcaagac | tgttggactg | gattccaagt | 9120 |
| agttccatgg | ccgcggacgc | gtctctaaag | accttccact | tgtccgctgt | cttgccttgt | 9180 |
| ttgatatcgg | ccagcgccgt | ctggcgccgc | acaagcgcaa | gcgtcattgg | ccgccgcccg | 9240 |
| aatggcgtcg | ttacacttcc | tgtctgcatc | atctttcacc | tttcagcagg | caaaggaaat | 9300 |
| cagctcacca | aaacggcgct | aaaaactctt | gacgaggatt | cgaggaaatg | cgattctgtt | 9360 |
| cgcgctagag | agacagaagg | gcttccgcga | cggcgacgtt | gaggggctc | ttttcttttg | 9420 |
| cggtttactc | tccccgtttc | cgttggttct | cagcgtggta | cgcttgatac | agcgctggca | 9480 |
| catgatcgag | cacgaaggtc | gcaaaatcgg | gcgtcgcctt | cctgtcaatc | gtgatttcca | 9540 |
| gtttggcctt | gctctgcgtc | acctgtgcaa | ttctggtgcc | gtctggggtg | gccatgacct | 9600 |
| cgggaagtcc | acgcgcaacc | cgactgggct | tcagactagc | gatcaccgcc | ttgaatcgtt | 9660 |
| ctgccgatgg | cagcgcttga | acttcctccg | acatagcata | tttagccacg | tcggccggtg | 9720 |
| aagaaacttt | ctcaatcagc | tcggcaagtt | gttgccaact | cggccgtcca | acaccaggag | 9780 |
| cggcaccaat | agcatcggtc | agttcagagg | ggagggcgtc | gacgagcaga | agcatcttgg | 9840 |
| acaaattgct | cttgtcgatc | gacatcgcgg | cgatgacaat | ctctcgagaa | aactgcctgt | 9900 |
| tcaggcgatg | tgcgaagcgc | gccttttcga | tgaaggtaag | atcttcgcgc | tcattgtttt | 9960 |
| cctgaccctg | tgctacgacc | acttgctcgt | ccgtcagttc | gcgaacgacc | gctctgaccg | 10020 |
| gaagtccgag | ttctgaaacg | cgcgtagcc | ggcggtggcc | gaaggcaacc | tgatatcggc | 10080 |
| ccggctggct | cggatgcggt | cgcacaagga | ttgggacttg | ctgtccttgt | tcccggatcg | 10140 |
| aagtaaggag | cccgtcaatg | tcccctcgca | tacgatcctg | cacgaaagac | ggttctattg | 10200 |
| acgaggcatc | caactctatc | actgcctgac | cttcagcgag | acgccgctcg | atctcttcgg | 10260 |
| cacggctaag | acgatcgttt | tgctctcgca | gtgcgttacc | aatgttcgct | gtgagcttcg | 10320 |
| ttgccggatc | gcgctccttc | cttgttacgc | cgaggagcgg | catggagcgg | ttctttgccg | 10380 |
| tcctattgtc | ggcgggcgac | gtctcagggg | cgtcagttga | gacgccaagg | atgtgcttcc | 10440 |
| ggctcatgtg | ggcctacccc | atgctttttt | gatcagtgtt | tcgatctcgt | cgttgacggc | 10500 |

```
gttcatcgcc tccaaggctc gatcataggt cgagcgcgtg aacaggccac gctccacttc    10560
gaatagagtc tggttttgtca ggccagcgtc cgaaaccgcg gtggttttaa gcatcggaaa    10620
attgaggaca ttttcgccaa aaatcgaccg cagataacct accatttggt tctgtggtcc    10680
gtcgctcggt tcgaaacggg ttatcagata gcgcatccaa ttaaacttga acttggcgcc    10740
agcattctcg atttcacgca aaaggttcga tgtcattgcc agaaactggt tcatcgacat    10800
cacatccagc atctgcggat ggaccgtgac aagaatggac gtcgccgcag tcaatgcgga    10860
tagcgtgaga tacccaagct ggggagggca gtcgatgacc acgacgtcat agttatccgc    10920
gatatcttca attacttggc tgatgcgacc ataaagagc gtgtcgccct ctttgcggtt    10980
catcagcgcg cgtggcgtat cgtgttcaaa ctccatcagc tcaaggttac caggaatcag    11040
gtggaggtcg ggaatgtaag tccctcggac gactcgttcg attgccacct gctcatcatc    11100 taccttata gcgccgtaga gcgtttcgtt cgggccaacg tccgtctccg gttggctccc    11160
aaagagtgca gaaaggctcg cttgaggatc gagatcaatg ccaagactc gatatccgcg    11220 catagcgagg tactgcgcca gatgcgcggc ggtggtggtc ttacccgacc caccttttgaa    11280 attcatcaca gagataacct gaagctgctc gccgcctcga cgatgtggca ggtagcgccg    11340
gttcccgcgg ccgacctgat ccatatactt ccgaatcaca tggatatctt caattgagaa    11400
cattcgcctg ccacccgggc tcatgctaac attcaactct ggcatctcag acgcggtctg    11460
ccgtaaatat gactcgccaa cgccgagcag cttgacgcc tccgatggcc cgaatgttcg    11520
aatgcccttc tcggaatgcg gcgggaaaac cttaagatga tgtgcttgaa gttggctcga    11580
gagggcatcg gcatgacgct ccatcaaggc cgtcaaccct acaactacag gcgctgcttt    11640
taggacagac ttcgccatct caaacccatt ccttgccagt ggcgatattt ttcgcgaaac    11700
tggaaaagtt ccgccgctgg caattagcgc cgattctgct gttttgggcaa gagcttttag    11760 gttaacagaa ggttaacgcc ctcaggtcga aaaactccac ccaactgtta tttgtattta    11820
tttccaatgc cttagagaga ttgccatttg aatatgttca tgtattgttt tagtgataat    11880
cctacaatcg taacccaaaa agaggtcgcc ctctgcgcgc cgtcgtccaa tataggcgaa    11940
gtcacccttg cgactcaggc ggattctacc ttgtagga                            11978
```

<210> SEQ ID NO 9
<211> LENGTH: 12438
<212> TYPE: DNA
<213> ORGANISM: Artificial Sequence
<220> FEATURE:
<223> OTHER INFORMATION: Plasmid pPG361

<400> SEQUENCE: 9

```
tcccgcttcg ccggcgttaa ctcaagcgat tagatgcact aagcacataa ttgctcacag      60
ccaaactatc aggtcaagtc tgcttttatt atttttaagc gtgcataata agccctacac     120
aaattgggag atatatcatg catgaccaaa atcccttaac gtgagttttc gttccactga     180
gcgtcagacc ccgtagaaaa gatcaaagga tcttcttgag atcctttttt tctgcgcgta     240
atctgctgct tgcaaacaaa aaaaccaccg ctaccagcgg tggtttgttt gccggatcaa     300
gagctaccaa ctcttttttcc gaaggtaact ggcttcagca gagcgcagat accaaatact     360
gtccttctag tgtagccgta gttaggccac cacttcaaga actctgtagc accgcctaca     420
tacctcgctc tgctaatcct gttaccagtg gctgctgcca gtggcgataa gtcgtgtctt     480
accgggttgg actcaagacg atagttaccg gataaggcgc agcggtcggg ctgaacgggg     540
```

```
ggttcgtgca cacagcccag cttggagcga acgacctaca ccgaactgag atacctacag    600
cgtgagctat gagaaagcgc cacgcttccc gaagggagaa aggcggacag gtatccggta    660
agcggcaggg tcggaacagg agagcgcacg agggagcttc caggggggaaa cgcctggtat    720 ctttatagtc ctgtcgggtt tcgccacctc tgacttgagc gtcgattttt gtgatgctcg    780 tcagggggc ggagcctatg gaaaaacgcc agcaacgcgg cctttttacg gttcctggcc     840
ttttgctggc cttttgctca catgttcttt cctgcgttat ccctgattc tgtggataac     900 cgtattaccg cctttgagtg agctgatacc gctcgccgca gccgaacgac cgagcgcagc    960
gagtcagtga gcgaggaagc ggaagagcgc ctgatgcggt attttctcct tacgcatctg   1020
tgcggtattt cacaccgcat atggtgcact ctcagtacaa tctgctctga tgccgcatag   1080
ttaagccagt atacactccg ctatcgctac gtgactgggt catggctgcg ccccgacacc   1140
cgccaacacc cgctgacgcg ccctgacggg cttgtctgct cccggcatcc gcttacagac   1200
aagctgtgac cgtctccggg agctgcatgt gtcagaggtt ttcaccgtca tcaccgaaac   1260
gcgcgaggca gggtgccttg atgtgggcgc cggcggtcga gtggcgacgg cgcggcttgt   1320
ccgcgccctg gtagagcccg ggcgggtgtt ctgtcgtctc gttgtacaac gaaatccatt   1380
cccattccgc gctcaagatg gcttcccctc ggcagttcat cagggctaaa tcaatctagc   1440
cgacttgtcc ggtgaaatgg gctgcactcc aacagaaaca atcaaacaaa catacacagc   1500
gacttattca cacgagctca aattacaacg gtatatatcc tgccagtcag catcatcaca   1560
ccaaaagtta ggcccgaata gtttgaaatt agaaagctcg caattgaggt ctacaggcca   1620
aattcgctct tagccgtaca atattactca ccggtgcgat gccccccatc gtaggtgaag   1680
gtggaaatta atgatccatc ttgtctagag gcgcgccagg cctccatctt gaaagaaata   1740
tagtttaaat atttattgat aaaataagtc aggtattata gtccaagcaa aaacataatt   1800
tattgatgca aagtttaaat tcagaaatat ttcataact gattatatca gctggtacat    1860
tgccgtagat gaaagactga gtgcgatatt atgtgtaata cataaattga tgatatagct   1920
agcttagctc atcgggccta ggtcattgtt tgcctccctg ctgcggtttt tcaccgaagt   1980
tcatgccagt ccagcgtttt tgcagcagaa aagccgccga cttcggtttg cggtcgcgag   2040
tgaagatccc tttcttgtta ccgccaacgc gcaatatgcc ttgcgaggtc gcaaaatcgg   2100
cgaaattcca tacctgttca ccgacgacgg cgctgacgcg atcaaagacg cggtgataca   2160
tatccagcca tgcacactga tactcttcac tccacatgtc ggtgtacatt gagtgcagcc   2220
cggctaacgt atccacgccg tattcggtga tgataatcgg ctgatgcagt ttctcctgcc   2280
aggccagaag ttcttttttcc agtaccttct ctgccgtttc caaatcgccg cttttggacat   2340 accatccgta ataacggttc aggcacagca catcaaagag atcgctgatg gtatcggtgt   2400
gagcgtcgca gaacattaca ttgacgcagg tgatcggacg cgtcgggtcg agtttacgcg   2460
ttgcttccgc cagtggcgcg aaatattccc gtgcaccttg cggacgggta tccggttcgt   2520
tggcaatact ccacatcacc acgcttgggt ggttttttgtc acgcgctatc agctctttaa   2580
tcgcctgtaa gtgcgcttgc tgagtttccc cgttgactgc ctcttcgctg tacagttctt   2640
tcggcttgtt gcccgcttcg aaaccaatgc ctaaagagag gttaaagccg acagcagcag   2700
tttcatcaat caccacgatg ccatgttcat ctgcccagtc gagcatctct tcagcgtaag   2760
ggtaatgcga ggtacggtag gagttggccc caatccagtc cattaatgcg tggtcgtgca   2820
ccatcagcac gttatcgaat ccttttgccac gcaagtccgc atcttcatga cgaccaaagc   2880
cagtaaagta gaacggtttg tggttaatca ggaactgttc gcccttcact gccactgacc   2940
```

```
ggatgccgac gcgaagcggg tagatatcac actctgtctg gcttttggct gtgacgcaca    3000
gttcatagag ataaccttca cccgttgcc agaggtgcgg attcaccact tgcaaagtcc     3060
cgctagtgcc ttgtccagtt gcaaccacct gttgatccgc atcacgcagt tcaacgctga    3120
catcaccatt ggccaccacc tgccagtcaa cagacgcgtg gttacagtct tgcgcgacat    3180
gcgtcaccac ggtgatatcg tccacccagg tgttcggcgt ggtgtagagc attacgctgc    3240
gatggattcc ggcatagtta agaaatcat ggaagtaaga ctgcttttc ttgccgtttt      3300 cgtcggtaat caccattccc ggcgggatag tctgccagtt cagttcgttg ttcacacaaa    3360
cggtgatacg tacacttttc ccggcaataa catacggcgt gacatcggct tcaaatggcg    3420
tatagccgcc ctgatgctcc atcacttcct gattattgac ccacactttg ccgtaatgag    3480
tgaccgcatc gaaacgcagc acgatacgct ggcctgccca acctttcggt ataaagactt    3540
cgcgctgata ccagacgttg cccgcataat tacgaatatc tgcatcggcg aactgatcgt    3600
taaaactgcc tggcacagca attgcccggc tttcttgtaa cgcgctttcc caccaacgct    3660
gatcaattcc acagttttcg cgatccagac tgaatgccca caggccgtcg agttttttga    3720
tttcccgggt tggggtttct acctgaatta atttaccacg gttaatactc agatcaagat    3780
ggtaaaaaaa tggcggtaag attaatctgc acactgtaat taataatgta ccggacgtaa    3840
catatgaagc ttagccatgg gtgatttcag cgtgtcctct ccaaatgaaa tgaacttcct    3900
tatatagagg aagggtcttg cgaaggatag tgggattgtg cgtcatccct tacgtcagtg    3960
gagatatcac atcaatccac ttgctttgaa gacgtggttg gaacgtcttc tttttccacg    4020
atgctcctcg tgggtggggg tccatctttg ggaccactgt cggcagaggc atcttgaacg    4080
atagcctttc ctttatcgca atgatggcat ttgtagtgcc accttccttt tctactgtcc    4140
ttttgatgaa gtgacagata ggatcgggaa ttaattcgga tccgtacggc gcgccgcgcc    4200
atttaaatca cgtgcgtacg ctcgagtcac gctgccgcaa gcactcaggg cgcaagggct    4260
gctaaaggaa gcggaacacg tagaaagcca gtccgcagaa acggtgctga ccccggatga    4320
atgtcagcta ctgggctatc tggacaaggg aaaacgcaag cgcaaagaga aagcaggtag    4380
cttgcagtgg gcttacatgg cgatagctag actgggcggt tttatggaca gcaagcgaac    4440
cggaattgcc agctggggcg ccctctggta aggttggaa gccctgcaaa gtaaactgga    4500
tggctttctt gccgccaagg atctgatggc gcagggatc aagatcatga gcggagaatt    4560
aagggagtca cgttatgacc cccgccgatg acgcgggaca agccgtttta cgtttggaac    4620
tgacagaacc gcaacgttga aggagccact cagccgcggg tttctggagt ttaatgagct    4680
aagcacatac gtcagaaacc attattgcgc gttcaaaagt cgcctaaggt cactatcagc    4740
tagcaaatat ttcttgtcaa aaatgctcca ctgacgttcc ataaattccc ctcggtatcc    4800
aattagagtc tcatattcac tctcaatccg tataccatgg ctaagcttat gaaaaagcct    4860
gaactcaccg cgacgtctgt cgagaagttt ctgatcgaaa agttcgacag cgtctccgac    4920
ctgatgcagc tctcggaggg cgaagaatct cgtgctttca gcttcgatgt aggagggcgt    4980
ggatatgtcc tgcgggtaaa tagctgcgcc gatggtttct acaaagatcg ttatgtttat    5040
cggcactttg catcggccgc gctcccgatt ccggaagtgc ttgacattgg ggcattcagc    5100
gagagcctga cctattgcat ctcccgccgt gcacagggtg tcacgttgca agacctgcct    5160
gaaaccgaac tgcccgctgt tctgcagccg gtcgcggagg ccatggatgc gatcgctgcg    5220
gccgatctta gccagacgag cgggttcggc ccattcggac cgcaaggaat cggtcaatac    5280
```

-continued

```
actacatggc gtgatttcat atgcgcgatt gctgatcccc atgtgtatca ctggcaaact    5340
gtgatggacg acaccgtcag tgcgtccgtc gcgcaggctc tcgatgagct gatgctttgg    5400
gccgaggact gccccgaagt ccggcacctc gtgcacgcgg atttcggctc caacaatgtc    5460
ctgacggaca atggccgcat aacagcggtc attgactgga gcgaggcgat gttcggggat    5520
tcccaatacg aggtcgccaa catcttcttc tggaggccgt ggttggcttg tatggagcag    5580
cagacgcgct acttcgagcg gaggcatccg gagcttgcag gatcgccgcg gctccgggcg    5640
tatatgctcc gcattggtct tgaccaactc tatcagagct tggttgacgg caatttcgat    5700
gatgcagctt gggcgcaggg tcgatgcgac gcaatcgtcc gatccggagc cgggactgtc    5760
gggcgtacac aaatcgcccg cagaagcgcg gccgtctgga ccgatggctg tgtagaagta    5820
ctcgccgata gtggaaaccg acgccccagc actcgtccga gggcaaagga atagaattcc    5880
taggcaactc tcctggcgca ccatcgtcgg ctacagcctc gggaattgct accgagctcg    5940
aatttccccg atcgttcaaa catttggcaa taaagtttct taagattgaa tcctgttgcc    6000
ggtcttgcga tgattatcat ataatttctg ttgaattacg ttaagcatgt aataattaac    6060
atgtaatgca tgacgttatt tatgagatgg gttttatga ttagagtccc gcaattatac    6120
atttaatacg cgatagaaaa caaaatatag cgcgcaaact aggataaaatt atcgcgcgcg    6180
gtgtcatcta tgttactaga tcgggaggcc tcacgtgggc cctattttat aataacgctg    6240
cggacatcta cattttgaa ttgaaaaaaa attggtaatt actctttctt tttctccata    6300
ttgaccatca tactcattgc tgatccatgt agatttcccg gacatgaagc catttacaat    6360
tgaatatatc ctgccgccgc tgccgctttg cacccggtgg agcttgcatg ttggtttcta    6420
cgcagaactg agccggttag gcagataatt tccattgaga actgagccat gtgcaccttc    6480
cccccaacac ggtgagcgac ggggcaacgg agtgatccac atgggacttt taaacatcat    6540
ccgtcggatg gcgttgcgag agaagcagtc gatccgtgag atcagccgac gcagcccggg    6600
ctgaggtctg cctcgtgaag aaggtgttgc tgactcatac caggcctgaa tcgccccatc    6660
atccagccag aaagtgaggg agccacggtt gatgagagct ttgttgtagg tggaccagtt    6720
ggtgattttg aacttttgct ttgccacgga acggtctgcg ttgtcgggaa gatgcgtgat    6780
ctgatccttc aactcagcaa aagttcgatt tattcaacaa agccgccgtc ccgtcaagtc    6840
agcgtaatgc tctgccagtg ttacaaccaa ttaaccaatt ctgattagaa aaactcatcg    6900
agcatcaaat gaaactgcaa tttattcata tcaggattat caataccata tttttgaaaa    6960
agccgtttct gtaatgaagg agaaaactca ccgaggcagt tccataggat ggcaagatcc    7020
tggtatcggt ctgcgattcc gactcgtcca acatcaatac aacctattaa tttcccctcg    7080
tcaaaaataa ggttatcaag tgagaaatca ccatgagtga cgactgaatc cggtgagaat    7140
ggcaacagct tatgcatttc tttccagact tgttcaacag gccagccatt acgtcgtca    7200
tcaaaatcac tcgcatcaac caaaccgtta ttcattcgtg attgcgcctg agcgagacga    7260
aatacgcgat cgctgttaaa aggacaatta caaacaggaa tcgaatgcaa ccggcgcagg    7320
aacactgcca gcgcatcaac aatattttca cctgaatcag gatattcttc taatacctgg    7380
aatgctgttt tcccggggat cgcagtggtg agtaaccatg catcatcagg agtacggata    7440
aaatgcttga tggtcggaag aggcataaat tccgtcagcc agtttagtct gaccatctca    7500
tctgtaacat cattggcaac gctaccttg ccatgtttca gaaacaactc tggcgcatcg    7560
ggcttcccat acaatcgata gattgtcgca cctgattgcc cgacattatc gcgagcccat    7620
ttatacccat ataaatcagc atccatgttg gaatttaatc gcggcctcga gcaagacgtt    7680
```

-continued

```
tcccgttgaa tatggctcat aacacccctt gtattactgt ttatgtaagc agacagtttt    7740
attgttcatg atgatatatt tttatcttgt gcaatgtaac atcagagatt ttgagacaca    7800
acgaagcttt ctgagccgcc gattttcctc ctcgagttgg atgaactcgc cgagttcatc    7860
gtcaactgaa acagacacgg ccggattctg tgagacaggt tgaaccgcag ctctcttcca    7920
ttgataatag gtctgaacgg aaatacccac gatcttaacg cgtccttca aggttgcgcc     7980 gccagcgacc tgagcttcga tttgaccgat cttctccagt tttttctcggt tgctgaggcc   8040 gcgggttttc ggcttcacgg atttgaacga tcccgtgcgg gctgtttcgg ctggtgcttt    8100
ctttgctctt ctacctctag gagcagccgg ctcaacttcg gcagcagcag taccgtccgg    8160
cggattctgg atctcttcgt cagccattaa tcgtcctctg tgtgggttat tgctttgtct    8220
gccagctcga tccaagagtc aacgtttgtg cctagggcag taaataggca gtgctccgcg    8280
actacatgcc tcgccggca aaataccgcc gcatgtagag caggctctcc ttcacgatca     8340
acgatcggca tggggccttc gtgcttgttg agtaatgtta tcgctcccat cagagcacgc    8400
ttggtactcc gggaatcgga tggtctgtcg atcatccaaa aaacgctcat gttttcaacc    8460
tattaggtct gtggtcagct gaccacagac catcctgctc catactcgct aattctagcc    8520
aaaccgcaac gtccctgcc cgctagcctt caagagcgcc attatcatcg ggccaagtga     8580
aaacttcccg agctcgctcc gccgtgtcag atctcggaga tagccccggg gcgaattgat    8640
gaagttcgct cgctccaaaa tgcacgccat cgctgctgcc gcattctccg gtcccattgc    8700
ctcacacgcg tcttggtaag ccgacgggct gaccccagc atagaccgaa ccaccaccgc     8760
agccgacatg aggtcacgcc agctagcaac cgcaccgctc ggcccataat tgccaatggt    8820
cgggcatgct ttcaggatca tcccgagggg gaacgctttt atcggctcgc tccttgcccg    8880
gtctatttca ctcggcttag cgccctgctc cttttcagag cgaggttcaa gttcattaac    8940
ggattcgggt tttgaattct gtatgtgctg ctcgctctgg gcagcattgg tgctattatt    9000
ttctgaattg tctctaattt ccaaccggtt gattatctct tcctggagca tccacatctc    9060
ttcgagaatt gactctacat cagcaagcgt cggggcgcgt ggaattctac ccacaagttc    9120
cacatagact tcctcgacag cttgccagtc gccctccgct ccctcttcca tagctgccgt    9180
aattagcttc cgaacgtccc gtcggcaaat cgtcagactt tctttggcca tcctgaatgc    9240
tgctcgatcg gccatcacct gctgtgccat catccgctagc tcttcggacc gcgcgagaag   9300
cggagacaaa tcgaagccaa acgcgcgctc gatctgacca gcgccatcct tacgagcgta    9360
acgctttccg ttggcgctat ccttccggac gatcaagcct gactccacga gcatggcgat    9420
gtgcctacgc aaagtcgcgc cagccatccc atgcgcccga agggcaagct gagcattcga    9480
cgggaagacg atcagctgtg cctcctgacg caactccgtt tccgggtgaa agctcaatag    9540
cgcatcaagg acggcaagac tgttggactg gattccaagt agttccatgg ccgcggacgc    9600
gtctctaaag accttccact tgtccgctgt cttgccttgt ttgatatcgg ccagcgccgt    9660
ctggcgccgc acaagcgcaa gcgtcattgg ccgccgcccg aatggcgtcg ttacacttcc    9720
tgtctgcatc atctttcacc tttcagcagg caaaggaaat cagctcacca aaacggcgct    9780
aaaaactctt gacgaggatt cgaggaaatg cgattctgtt cgcgctagag agacagaagg    9840
gcttccgcga cggcgacgtt gaggggggctc ttttcttttg cggtttactc tccccgtttc    9900
cgttggttct cagcgtggta cgcttgatac agcgctggca catgatcgag cacgaaggtc    9960
gcaaaatcgg gcgtcgcctt cctgtcaatc gtgatttcca gtttggcctt gctctgcgtc   10020
```

-continued

```
acctgtgcaa ttctggtgcc gtctggggtg gccatgacct cgggaagtcc acgcgcaacc    10080
cgactgggct tcagactagc gatcaccgcc ttgaatcgtt ctgccgatgg cagcgcttga    10140
acttcctccg acatagcata tttagccacg tcggccggtg aagaaacttt ctcaatcagc    10200
tcggcaagtt gttgccaact cggccgtcca acaccaggag cggcaccaat agcatcggtc    10260
agttcagagg ggagggcgtc gacgagcaga agcatcttgg acaaattgct cttgtcgatc    10320
gacatcgcgg cgatgacaat ctctcgagaa aactgcctgt tcaggcgatg tgcgaagcgc    10380
gccttttcga tgaaggtaag atcttcgcgc tcattgtttt cctgaccctg tgctacgacc    10440
acttgctcgt ccgtcagttc gcgaacgacc gctctgaccg gaagtccgag ttctgaaacg    10500
gcgcgtagcc ggcggtggcc gaaggcaacc tgatatcggc ccggctggct cggatgcggt    10560
cgcacaagga ttgggacttg ctgtccttgt tcccggatcg aagtaaggag cccgtcaatg    10620
tcccctcgca tacgatcctg cacgaaagac ggttctattg acgaggcatc caactctatc    10680
actgcctgac cttcagcgag acgccgctcg atctcttcgg cacggctaag acgatcgttt    10740
tgctctcgca gtgcgttacc aatgttcgct gtgagcttcg ttgccggatc gcgctccttc    10800
cttgttacgc cgaggagcgg catggagcgg ttctttgccg tcctattgtc ggcgggcgac    10860
gtctcagggg cgtcagttga gacgccaagg atgtgcttcc ggctcatgtg ggcctacccc    10920
atgcttttttt gatcagtgtt tcgatctcgt cgttgacggc gttcatcgcc tccaaggctc    10980
gatcataggt cgagcgcgtg aacaggccac gctccacttc gaatagagtc tggtttgtca    11040
ggccagcgtc cgaaaccgcg gtggttttaa gcatcggaaa attgaggaca ttttcgccaa    11100
aaatcgaccg cagataacct accatttggt tctgtggtcc gtcgctcggt tcgaaacggg    11160
ttatcagata gcgcatccaa ttaaacttga acttggcgcc agcattctcg atttcacgca    11220
aaaggttcga tgtcattgcc agaaactggt tcatcgacat cacatccagc atctgcggat    11280
ggaccgtgac aagaatggac gtcgccgcag tcaatgcgga tagcgtgaga tacccaagct    11340
ggggagggca gtcgatgacc acgacgtcat agttatccgc gatatcttca attacttggc    11400
tgatgcgacc ataaaagagc gtgtcgccct ctttgcggtt catcagcgcg cgtggcgtat    11460
cgtgttcaaa ctccatcagc tcaaggttac caggaatcag gtggaggtcg ggaatgtaag    11520
tccctcggac gactcgttcg attgccacct gctcatcatc ataccttata gcgccgtaga    11580
gcgtttcgtt cgggccaacg tccgtctccg gttggctccc aaagagtgca gaaaggctcg    11640
cttgaggatc gagatcaatg gccaagactc gatatccgcg catagcgagg tactgcgcca    11700
gatgcgcggc ggtggtggtc ttacccgacc caccctttgaa attcatcaca gagataaccct    11760
gaagctgctc gccgcctcga cgatgtggca ggtagcgccg gttcccgcgg ccgacctgat    11820
ccatatactt ccgaatcaca tggatatctt caattgagaa cattcgcctg ccacccgggc    11880
tcatgctaac attcaactct ggcatctcag acgcggtctg ccgtaaatat gactcgccaa    11940
cgccgagcag cttggacgcc tccgatggcc cgaatgttcg aatgcccttc tcggaatgcg    12000
gcgggaaaac cttaagatga tgtgcttgaa gttggctcga gagggcatcg gcatgacgct    12060
ccatcaaggc cgtcaaccct acaactacag gcgctgcttt taggacagac ttcgccatct    12120
caaacccatt ccttgccagt ggcgatattt tcgcgaaac tggaaaagtt ccgccgctgg    12180
caattagcgc cgattctgct gtttgggcaa gagcttttag gttaacagaa ggttaacgcc    12240
ctcaggtcga aaaactccac ccaactgtta tttgtattta tttccaatgc cttagagaga    12300
ttgccatttg aatatgttca tgtattgttt tagtgataat cctacaatcg taacccaaaa    12360
agaggtcgcc ctctgcgcgc cgtcgtccaa tataggcgaa gtcacccttg cgactcaggc    12420
```
ggattctacc ttgtagga                                                   12438

<210> SEQ ID NO 10
<211> LENGTH: 4297
<212> TYPE: DNA
<213> ORGANISM: Artificial Sequence
<220> FEATURE:
<223> OTHER INFORMATION: Plasmid pPG354

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt tatccccac gtgcgtacga    420
tcatgagcgg agaattaagg gagtcacgtt atgaccccg ccgatgacgc gggacaagcc    480
gttttacgtt tggaactgac agaaccgcaa cgttgaagga gccactcagc cgcgggtttc    540
tggagtttaa tgagctaagc acatacgtca gaaaccatta ttgcgcgttc aaaagtcgcc    600
taaggtcact atcagctagc aaatatttct tgtcaaaaat gctccactga cgttccataa    660
attcccctcg gtatccaatt agagtctcat attcactctc aatccaaata atctgcagat    720
cctagacgat cgtttcgcca tggctaagct tatgaaaaag cctgaactca ccgcgacgtc    780
tgtcgagaag tttctgatcg aaaagttcga cagcgtctcc gacctgatgc agctctcgga    840
gggcgaagaa tctcgtgctt tcagcttcga tgtaggaggg cgtggatatg tcctgcgggt    900
aaatagctgc gccgatggtt tctacaaaga tcgttatgtt tatcggcact ttgcatcggc    960
cgcgctcccg attccggaag tgcttgacat tggggaattc agcgagagcc tgacctattg   1020
catctcccgc cgtgcacagg gtgtcacgtt gcaagacctg cctgaaaccg aactgcccgc   1080
tgttctgcag ccggtcgcgg aggccatgga tgcgatcgct gcggccgatc ttagccagac   1140
gagcgggttc ggcccattcg gaccgcaagg aatcggtcaa tacactacat ggcgtgattt   1200
catatgcgcg attgctgatc cccatgtgta tcactggcaa actgtgatgg acgacaccgt   1260
cagtgcgtcc gtcgcgcagg ctctcgatga gctgatgctt tgggccgagg actgccccga   1320
agtccggcac ctcgtgcacg cggatttcgg ctccaacaat gtcctgacgg acaatggccg   1380
cataacagcg gtcattgact ggagcgaggc gatgttcggg gattcccaat acgaggtcgc   1440
caacatcttc ttctggaggc cgtggttggc ttgtatggag cagcagacgc gctacttcga   1500
gcggaggcat ccggagcttg caggatcgcc gcggctccgg gcgtatatgc tccgcattgg   1560
tcttgaccaa ctctatcaga gcttggttga cggcaatttc gatgatgcag cttgggcgca   1620
gggtcgatgc gacgcaatcg tccgatccgg agccgggact gtcggcgta cacaaatcgc   1680
ccgcagaagc gcggccgtct ggaccgatgg ctgtgtagaa gtactcgccg atagtggaaa   1740
ccgacgcccc agcactcgtc cgagggcaaa ggaatagaat tcctaggatc gttcaaacat   1800
ttggcaataa agtttcttaa gattgaatcc tgttgccggt cttgcgatga ttatcatata   1860
atttctgttg aattacgtta agcatgtaat aattaacatg taatgcatga cgttatttat   1920
gagatgggtt tttatgatta gagtcccgca attatacatt taatacgcga tagaaaacaa   1980
```

-continued

```
aatatagcgc gcaaactagg ataaattatc gcgcgcggtg tcatctatgt tactagatcg      2040
aggcctcacg tggggtatag cttggcgtaa tcatggtcat agctgtttcc tgtgtgaaat      2100
tgttatccgc tcacaattcc acacaacata cgagccggaa gcataaagtg taaagcctgg      2160
ggtgcctaat gagtgagcta actcacatta attgcgttgc gctcactgcc cgctttccag      2220
tcgggaaacc tgtcgtgcca gctgcattaa tgaatcggcc aacgcgcggg gagaggcggt      2280
ttgcgtattg ggcgctcttc cgcttcctcg ctcactgact cgctgcgctc ggtcgttcgg      2340
ctgcggcgag cggtatcagc tcactcaaag gcggtaatac ggttatccac agaatcaggg      2400
gataacgcag gaaagaacat gtgagcaaaa ggccagcaaa aggccaggaa ccgtaaaaag      2460
gccgcgttgc tggcgttttt ccataggctc cgcccccctg acgagcatca caaaaatcga      2520
cgctcaagtc agaggtggcg aaacccgaca ggactataaa gataccaggc gtttccccct      2580
ggaagctccc tcgtgcgctc tcctgttccg accctgccgc ttaccggata cctgtccgcc      2640
tttctccctt cgggaagcgt ggcgctttct catagctcac gctgtaggta tctcagttcg      2700
gtgtaggtcg ttcgctccaa gctgggctgt gtgcacgaac cccccgttca gcccgaccgc      2760
tgcgccttat ccggtaacta tcgtcttgag tccaacccgg taagacacga cttatcgcca      2820
ctggcagcag ccactggtaa caggattagc agagcgaggt atgtaggcgg tgctacagag      2880
ttcttgaagt ggtggcctaa ctacggctac actagaagga cagtatttgg tatctgcgct      2940
ctgctgaagc cagttacctt cggaaaaaga gttggtagct cttgatccgg caaacaaacc      3000
accgctggta gcggtggttt ttttgtttgc aagcagcaga ttacgcgcag aaaaaaagga      3060
tctcaagaag atcctttgat cttttctacg gggtctgacg ctcagtggaa cgaaaactca      3120
cgttaaggga ttttggtcat gagattatca aaaaggatct tcacctagat ccttttaaat      3180
taaaaatgaa gttttaaatc aatctaaagt atatatgagt aaacttggtc tgacagttac      3240
caatgcttaa tcagtgaggc acctatctca gcgatctgtc tatttcgttc atccatagtt      3300
gcctgactcc ccgtcgtgta gataactacg atacgggagg gcttaccatc tggccccagt      3360
gctgcaatga taccgcgaga cccacgctca ccggctccag atttatcagc aataaaccag      3420
ccagccggaa gggccgagcg cagaagtggt cctgcaactt tatccgcctc catccagtct      3480
attaattgtt gccgggaagc tagagtaagt agttcgccag ttaatagttt gcgcaacgtt      3540
gttgccattg ctacaggcat cgtggtgtca cgctcgtcgt ttggtatggc ttcattcagc      3600
tccggttccc aacgatcaag gcgagttaca tgatccccca tgttgtgcaa aaaagcggtt      3660
agctccttcg gtcctccgat cgttgtcaga agtaagttgg ccgcagtgtt atcactcatg      3720
gttatggcag cactgcataa ttctcttact gtcatgccat ccgtaagatg cttttctgtg      3780
actggtgagt actcaaccaa gtcattctga gaatagtgta tgcggcgacc gagttgctct      3840
tgcccggcgt caatacggga taataccgcg ccacatagca gaactttaaa agtgctcatc      3900
attggaaaac gttcttcggg gcgaaaactc tcaaggatct taccgctgtt gagatccagt      3960
tcgatgtaac ccactcgtgc acccaactga tcttcagcat cttttacttt caccagcgtt      4020
tctgggtgag caaaaacagg aaggcaaaat gccgcaaaaa agggaataag ggcgacacgg      4080
aaatgttgaa tactcatact cttcctttt  caatattatt gaagcattta tcagggttat      4140
tgtctcatga gcggatacat atttgaatgt atttagaaaa ataaacaaat aggggttccg      4200
cgcacatttc cccgaaaagt gccacctgac gtctaagaaa ccattattat catgacatta      4260
acctataaaa ataggcgtat cacgaggccc tttcgtc                              4297
```